US011058886B1

(12) United States Patent
Matloubian et al.

(10) Patent No.: US 11,058,886 B1
(45) Date of Patent: Jul. 13, 2021

(54) METHOD OF POLARIZATION CONTROL OF EVANESCENT WAVES FOR TREATING TUMORS

(71) Applicant: EVANESC THERAPEUTICS, INC., Canoga Park, CA (US)

(72) Inventors: Mehran Matloubian, Encino, CA (US); Timothy J. Brockett, Malibu, CA (US); Gregg A. Hollingsworth, Tempe, AZ (US)

(73) Assignee: EVANESC THERAPEUTICS, INC., Canoga Park, CA (US)

( * ) Notice: Subject to any disclaimer, the term of this patent is extended or adjusted under 35 U.S.C. 154(b) by 182 days.

(21) Appl. No.: 16/369,590

(22) Filed: Mar. 29, 2019

Related U.S. Application Data

(60) Provisional application No. 62/653,456, filed on Apr. 5, 2018, provisional application No. 62/653,459, filed on Apr. 5, 2018.

(51) Int. Cl.
*A61N 1/40* (2006.01)
*A61N 1/06* (2006.01)
*A61N 5/06* (2006.01)
*A61N 1/04* (2006.01)

(52) U.S. Cl.
CPC ............... *A61N 1/40* (2013.01); *A61N 1/06* (2013.01); *A61N 1/0404* (2013.01); *A61N 5/062* (2013.01)

(58) Field of Classification Search
CPC .......... A61N 1/40; A61N 1/06; A61N 1/0404; A61N 5/062
See application file for complete search history.

(56) References Cited

U.S. PATENT DOCUMENTS

| | | | |
|---|---|---|---|
| 4,822,470 A | 4/1989 | Chang | |
| 4,846,178 A | 7/1989 | Fuxue et al. | |
| 5,186,181 A | 2/1993 | Franconi et al. | |
| 5,540,681 A | 7/1996 | Strul et al. | |
| 6,868,289 B2 | 3/2005 | Palti | |
| 7,805,201 B2 | 9/2010 | Palti | |
| 8,684,901 B1 * | 4/2014 | Zabara | A61N 1/40 600/14 |
| 8,715,203 B2 | 5/2014 | Palti | |

* cited by examiner

*Primary Examiner* — Lindsey G Wehrheim
(74) *Attorney, Agent, or Firm* — Richard T. Ogawa; Ogawa P.C.

(57) ABSTRACT

Current cancer treatments such as surgery, radiation and chemotherapy have significant side-effects for the patients. New treatments are being developed to reduce these side-effects while giving doctors alternative methods to treat patients. This invention introduces a new method for treatment of malignant tumors including brain cancer, pancreatic cancer, lung cancer, and ovarian cancer. The method uses low-power RF wave to disrupt and kill cancer cells during mitosis resulting in shrinking the size of solid tumors. Direction of polarization of the electric field of the RF wave relative to the axis of division of the cancer cells has an impact on the ability of the RF wave in disrupting mitosis and killing the cancer cells. Since the orientation of the cancer cells in a tumor are random a method is needed to change the orientation of the applied RF wave spatially with time to maximize elimination of the cancer cells.

21 Claims, 25 Drawing Sheets

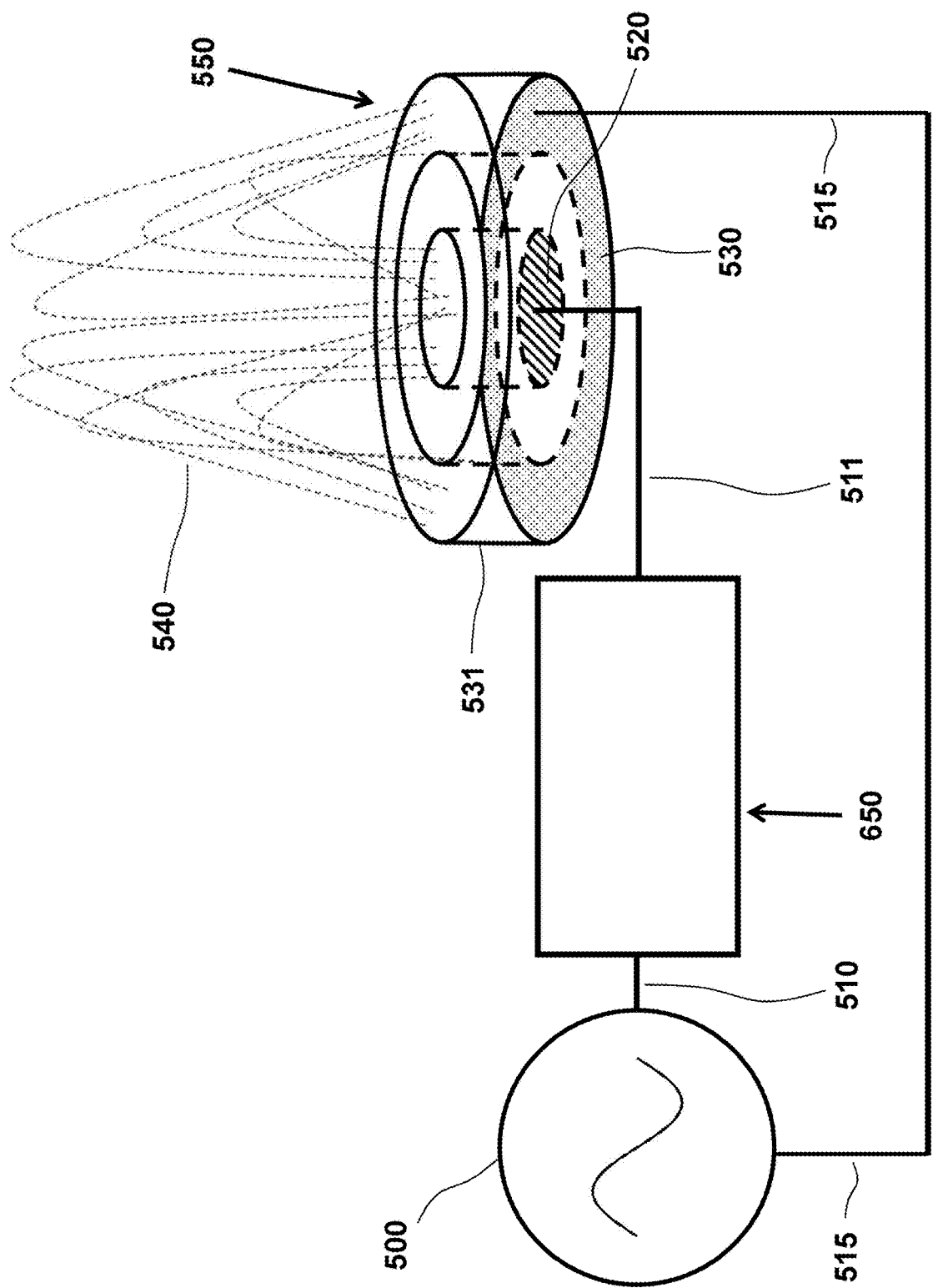

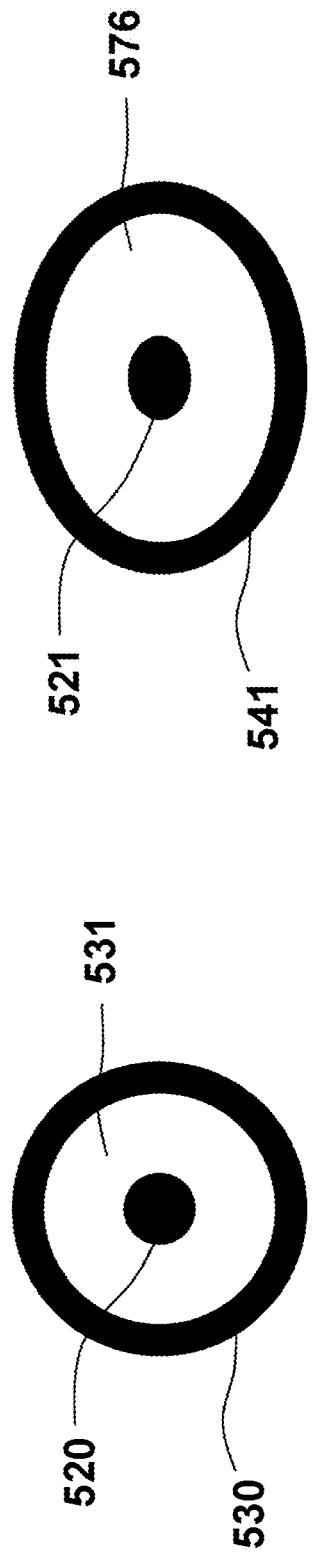
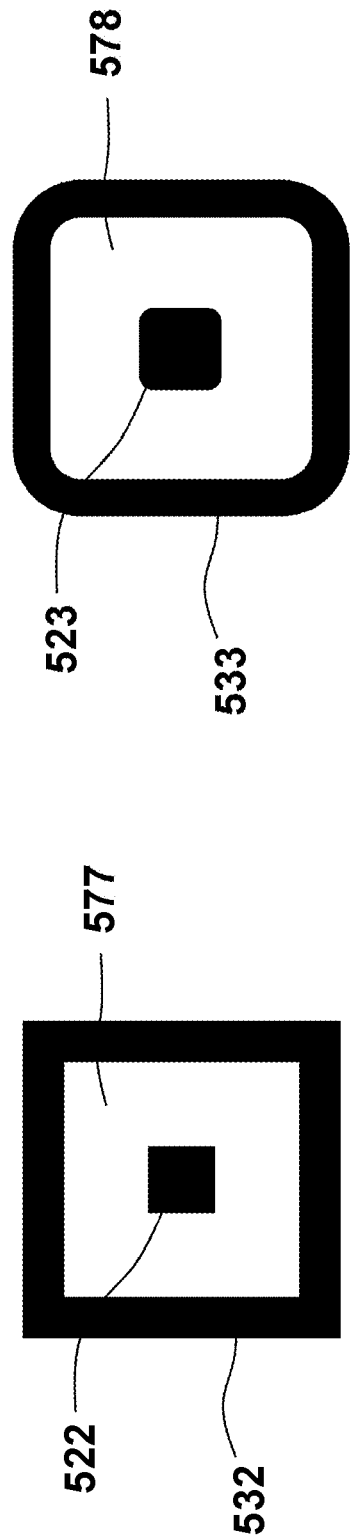
Figure 14A
Figure 14B
Figure 14C
Figure 14D

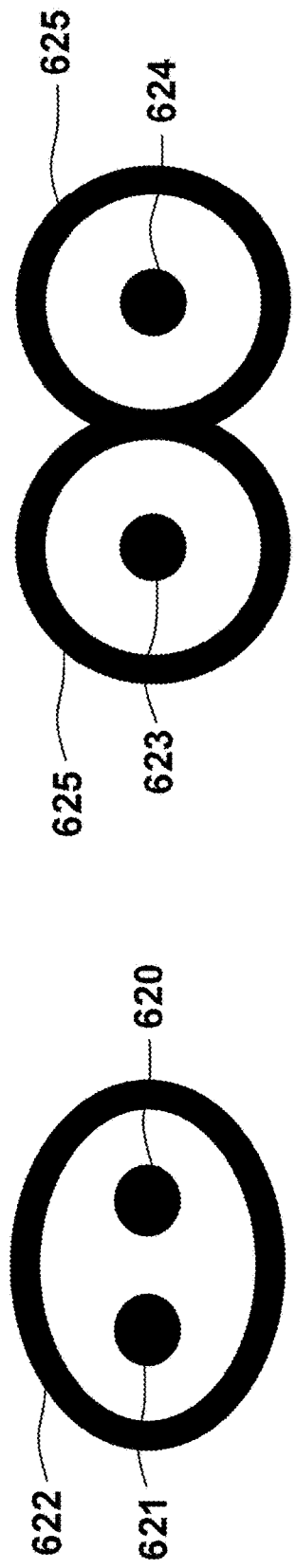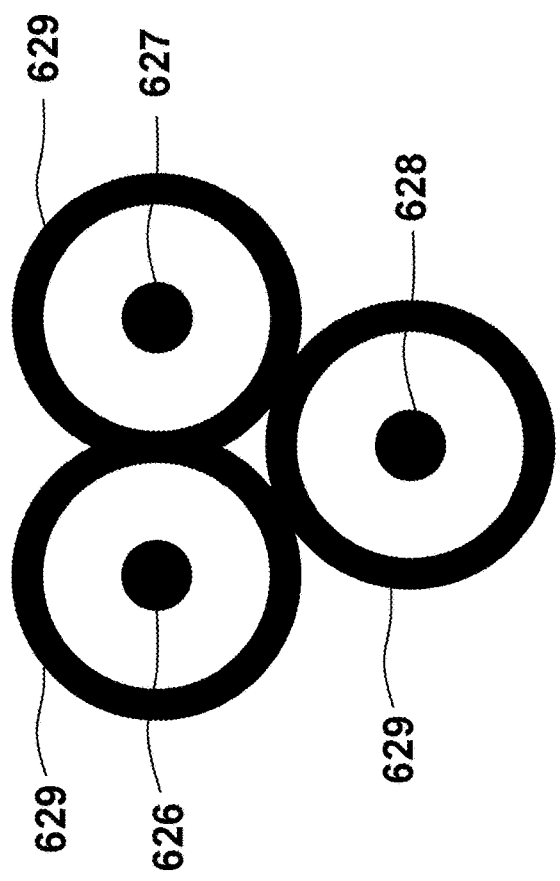
Figure 16A
Figure 16B
Figure 16C

METHOD OF POLARIZATION CONTROL OF EVANESCENT WAVES FOR TREATING TUMORS

CROSS-REFERENCES TO RELATED APPLICATIONS

This application claims priority to U.S. Provisional Patent Application No. 62/653,456, filed Apr. 5, 2018, entitled "METHOD OF POLARIZATION CONTROL OF EVANESCENT WAVES FOR TREATING TUMORS," and to U.S. Provisional Patent Application No. 62/653,459, filed Apr. 5, 2018, entitled "DYNAMIC POLARIZATION CONTROL OF EVANESCENT WAVES FOR TREATING TUMORS," commonly assigned and incorporated by reference herein for all purposes.

STATEMENT AS TO RIGHTS TO INVENTIONS MADE UNDER FEDERALLY SPONSORED RESEARCH OR DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

There are primarily three methods used to treat malignant solid tumors in cancer patients. The three methods consist of surgery, radiation, and chemotherapy. Each method has its own side-effects or drawbacks with limited efficacy for a number of solid tumor cancers including pancreatic cancer and lung cancer. Immunotherapy is another method currently under development for cancer treatment. Immunotherapy appears promising however it has worked successfully only in a small subset of patients with solid tumor cancers. Recently another method has shown promise for treatment of solid tumor cancers and has been approved by the FDA for treating glioblastoma (a certain type of brain cancer). The new method involves capacitively coupling low-power RF to the patients head in order to subject the tumor to electric fields (U.S. Pat. No. 7,805,201). The electric fields interfere with the dividing cancer cells during mitosis causing the cancer cells to die and the tumor to shrink. The electric fields do not impact non-dividing cells so there is no harmful impact to the non-dividing healthy cells and has no adverse side effect on the patient. Effectiveness of the electric fields in disrupting the division of the cancer cells depends on several factors including the frequency of the RF source, the magnitude of the electric fields in the tumor as well as the electrical conductivity and dielectric properties of the tumor (effective RF power density/dissipation in the tumor), and on the relative orientation (or polarization) of the electric fields and the axis of the dividing cells.

Different types of cancer cells respond to different frequencies of the RF source. For example, it has been demonstrated that for a number of glioblastoma cancer cells, a frequency of around 200 KHz is the optimum frequency to kill the cells while for lung cancer cells the optimum frequency has been demonstrated to be around 150 KHz. Although there is an optimum frequency for killing the cancer cells, in reality there is a range of frequencies around the optimum frequency that can be used for killing the cancer cells. So instead of using an RF source with a fixed frequency of 200 KHz for example, it is possible to use an RF source that periodically steps its frequency from 100 KHz to 300 KHz or sweeps its output frequency from 100 KHz to 300 KHz.

In order to kill the cancer cells, a minimum electric field of around 1 V/cm is desired inside the tumor. In addition, the conductivity of the tumor also has an impact with a higher conductivity tumor leading to higher RF power densities in the tumor. A minimum RF power density of around 1 mW/cm$^3$ is desired in the tumor; however, higher electric fields and higher RF power densities in the tumor will result in higher efficacy in killing cancer cells. The power density in the tumor is proportional to the square of the electric field in the tumor and is directly proportional to the conductivity of the tumor. So doubling the electric field in a tumor will increase RF power density in the tumor by a factor of four and a tumor with double the conductivity will have double the RF power density in the tumor.

In addition to the magnitude of the electric field, the effectiveness of killing cancer cells also depends on the orientation (polarization) of the electric field relative to the axis of dividing cells. In order to target more dividing cancer cells during treatment by capacitive coupling, two sets of electrodes are typically used to capacitively couple the electric fields in two different polarizations (typically the two polarizations are perpendicular to each other). Each electrode consists of an array of nine elements. A typical application for treating brain tumors would require four arrays of electrodes with a combined total of 36 elements. There are limitations and drawbacks in applying electric field to the tumor using capacitive coupling. The electrodes form a low series capacitance with the patient's head resulting in high series impedance (resistance) causing a significant amount of the voltage applied across the head to drop across this series impedance. In order to overcome this issue, a very high dielectric constant material is used between the metal electrode and the patient's skin to increase the value of the series capacitance and reduce the series impedance. While this reduces the amount of voltage drop across the series impedance, still a substantial part of the voltage applied drops across this series capacitor as well as across the healthy tissue between the electrode and the tumor reducing the voltage drop across the tumor itself and the ability to achieve higher electric fields of substantially more than 1 V/cm in the tumor. Another limitation of capacitive coupling is that the electrodes have to be in intimate contact with the patient's skin since any air gap between the electrodes and the patient's skin forms a low series capacitance that reduces the voltage drop across the tumor significantly. As a result, for brain cancer patients, the patient's head has to be shaved every few days and a new set of electrodes attached via an adhesive to the patient's head in order for the electrodes to make intimate contact with the skin (typically a conductive gel is used between the electrode and the patient's skin to assure a good contact with no air gaps). The use of adhesives to attach the electrodes for long period of times has caused skin irritation in some of the patients. Another limitation of capacitive coupling is that the RF power is applied to the complete head and not localized to the tumor, thus dissipating a significant amount of the RF power across parts of the head with no tumor. There is a limit as to how much power can be delivered before the skin of the patient is heated beyond a comfortable level. Due to this wasted RF energy as well as wasted power in the series capacitor, the amount of RF power that can be delivered specifically to the tumor is limited and prevents the ability to achieve much higher electric fields than 1 V/cm. As mentioned earlier, using capacitive coupling the electric fields are typically applied in two fixed polarizations orthogonal to each other, but the tumor is a three-dimensional object. The orientation of dividing cells in a tumor are random and can be in a direction perpendicular to the orientation of the two electric fields or may be oriented in a direction where the two electric fields that are applied will not disrupt the dividing cell. This can lead to a significant number of cells not being affected by the electric fields and allows the tumor to grow or not shrink as rapidly as possible. Clearly better approaches are needed to increase the effectiveness of RF electric fields to disrupt the dividing cells for treating tumors and provide better comfort for the patients.

BRIEF SUMMARY OF THE INVENTION

In this invention a novel apparatus for coupling RF power efficiently via evanescent waves to cancer tumors is described along with methods to vary the direction of the polarization of the evanescent waves coupled to the tumor. The apparatus consists of an RF source with one or more coupling elements (wave-launchers, antennas, apertures) that couple RF evanescent waves to part of the body with a tumor. The evanescent waves disrupt the cancer cells during mitosis (as the cells are dividing) causing the cancer cells to die and the tumor size to shrink over time. In one embodiment of this invention, the apparatus consists of an RF source connected to a coupling element through a wire or cable. The coupling element is designed and configured to launch evanescent waves at a desired frequency into the body and couple them efficiently to the cancer tumor. Using this approach, the evanescent waves can be used to target the tumor while significantly reducing RF energy in parts of the brain or body that does not have a tumor.

Another advantage of this invention is that in the case of brain cancer for example, it does not require a large array of 36 electrodes covering the head of the patient for treating brain cancer and heating the patient's head. The direction of the electric field is also not limited to only two directions in the typical case used in the treatment process. In this invention, utilizing three coupling elements, the evanescent waves can be applied in three perpendicular directions by exciting each coupling element independently. In addition, exciting all three coupling elements simultaneously and changing the amplitude and/or phase of the RF source input independently or simultaneously to the coupling elements, one can change the direction of the applied evanescent waves and the electric fields to target different parts of the tumor. Another advantage of this approach is that the electromagnetic waves are configured to bypass the series capacitance between the insulated electrodes and does not require the insulation to have a high dielectric constant as is required by capacitive coupling. This allows the system to operate more efficiently compared to capacitive coupling and is able to achieve higher electric fields inside the tumor at lower RF power levels. Furthermore, it is not necessary to have the coupling elements to be in intimate contact with the patient's skin allowing longer usage of the coupling elements and less discomfort for the patient's due to the use of adhesives that can cause skin irritation. The coupling element is able to couple RF energy to the patient's brain even if the patient has short hair so the patient does not have to shave his/hair every two to three days.

As mentioned above, the novel apparatus disclosed in this invention compared to the apparatus using capacitive coupling of electric fields has several advantages for treating cancer tumors. These include higher efficiency with less RF energy dissipated in healthy cells, achieving higher fields and RF power density in the tumor due to the ability to target the RF energy more precisely, operating at lower currents as well as dissipating less RF power, and the bypass of the low value series capacitance (high series impedance) that reduces the voltage drop across the tumor. Since the system operates more efficiently than capacitive coupling one can make portable systems that are more compact, lighter weight, with a longer lasting battery for the patient to use. In addition, the novel approach described reduces or eliminates heating the skin of the patient during the treatment as well as dissipated heat in the patient's body which reduces patient's discomfort particularly during warm weather. Furthermore, it reduces the number of electrodes/coupling elements needed to deliver the required RF power and eliminates the need for the electrode/coupling element to be in intimate contact with the patient's skin eliminating the need to shave the patient routinely as well as eliminates skin irritation caused by adhesives used to attach the electrodes to the patient's skin. Another advantage of this invention is that by using only three coupling elements the polarization of the applied field can be varied dynamically in three dimensions by controlling the amplitude and/or phase of the applied RF to each coupling element allowing the system to target more cells. With capacitive coupling two sets of electrodes have to be placed across from each other in order to apply the electric field in a particular direction. In most cases it is not practical to be able to place three sets of electrodes across part of the body in order to be able to control the polarization direction in three dimensions as a result the capacitive coupling systems are primarily limited to controlling polarization of the applied electric field in two dimensions.

In addition to brain cancer, this invention with the method described, has applications in treating other types of solid tumor cancers including but not limited to lung cancer, ovarian cancer, breast cancer, and pancreatic cancer. Furthermore, since this treatment has no side effects it can be combined with other cancer treatments, including radiation, surgery, chemotherapy, and immunotherapy, to increase overall treatment efficacy and increasing overall survival rate of the patients.

BRIEF DESCRIPTION OF THE DRAWINGS

FIG. 6A is a drawing of another embodiment of this invention. This embodiment is similar to the embodiment in FIG. 5A except a matching element or coupling device is inserted between the RF source and the coupling element in order to maximize coupling of the evanescent waves to the tumor.

FIG. 14A is a drawing of the cross section of a coupling element that is coaxial in design.

FIG. 14B is a drawing similar to FIG. 14A except the cross section of the coupling element is oval.

FIG. 14C is a drawing similar to FIG. 14A except the cross section of the coupling element is square.

FIG. 14D is a drawing similar to FIG. 14C except the corners of the square cross section are rounded.

FIG. 16A is a drawing of a different coupling element than the one shown in FIG. 14B consisting of two center conductors.

FIG. 16B is a drawing of a different coupling element consisting of two coupling elements similar to the coupling element shown in FIG. 15C.

FIG. 16C is a drawing of a different coupling element consisting of three coupling elements similar to the coupling element shown in FIG. 15C.

DETAILED DESCRIPTION OF THE INVENTION

Figure 1:
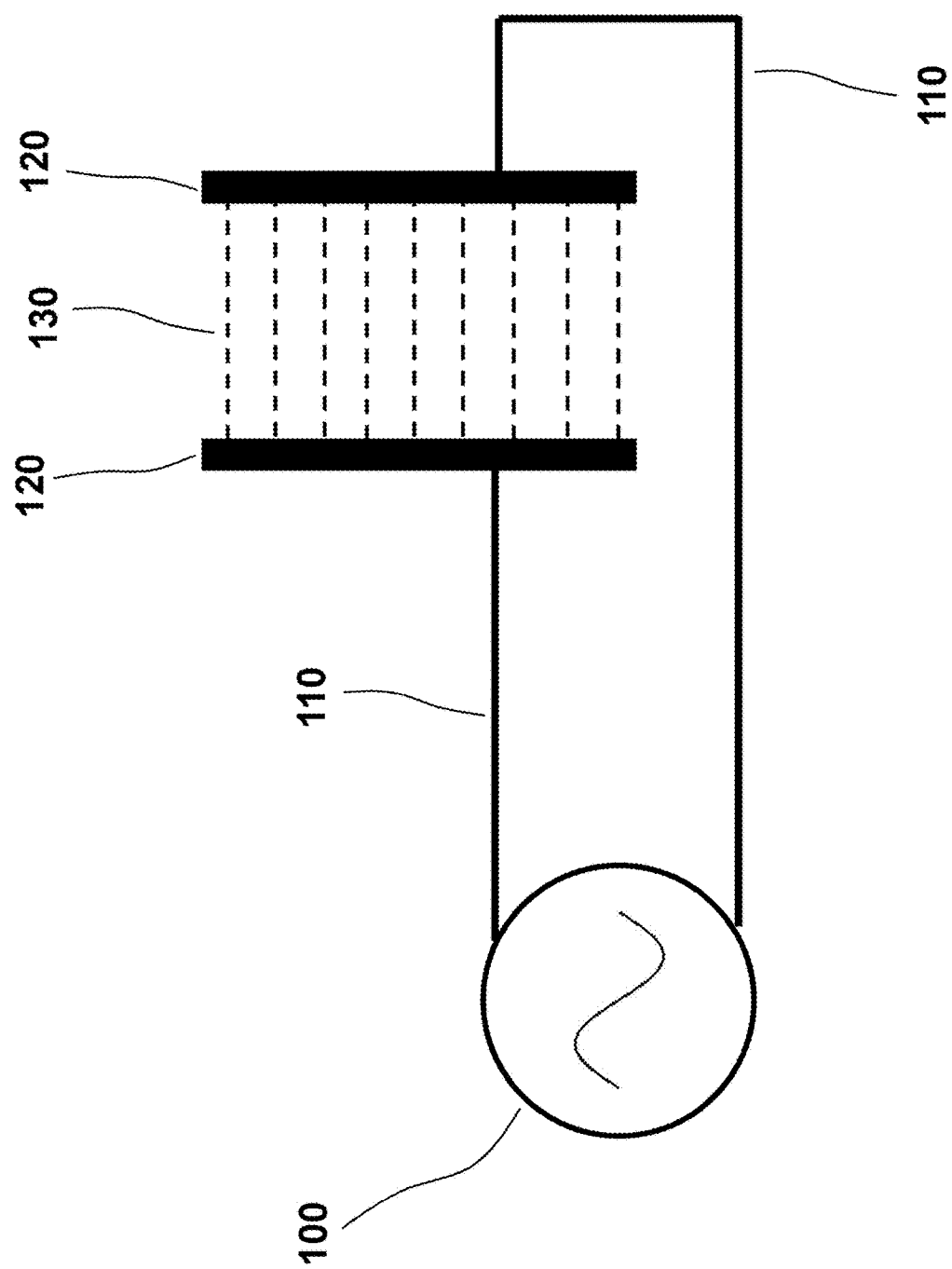
FIG. 1 is a drawing of the prior art of an apparatus for treating cancer tumors consisting of an RF source connected to two electrodes for capacitively applying electric field to a tumor.

The following description is presented to enable one of ordinary skill in the art to make and use the invention and to incorporate it in the context of particular applications. Various modifications, as well as a variety of uses in different applications will be readily apparent to those skilled in the art, and the general principles defined herein may be applied to a wide range of embodiments. Thus, the present invention is not intended to be limited to the embodiments presented, but is to be accorded the widest scope consistent with the principles and novel features disclosed herein.

In the following detailed description, numerous specific details are set forth in order to provide a more thorough understanding of the present invention. However, it will be apparent to one skilled in the art that the present invention may be practiced without necessarily being limited to these specific details.

Please note, if used, the labels left, right, front, back, top, bottom, forward, reverse, clockwise and counter clockwise have been used for convenience purposes only and are not intended to imply any particular fixed direction. Instead, they are used to reflect relative locations and/or directions between various portions of an object. Additionally, the terms "first" and "second" or other like descriptors do not necessarily imply an order, but should be interpreted using ordinary meaning.

In one embodiment of this invention the apparatus comprises of an RF source connected to a coupling element using wire or RF cable. The coupling element is designed to launch evanescent waves at a particular frequency or range of frequencies into the human body in the vicinity of a tumor and couple the evanescent waves into the tumor. The magnitude of the RF power is selected to be able to disrupt the cancer cells during mitosis causing the cancer cells to die and over time leading to the reduction in the size of the tumor. The coupling element can be in intimate contact with the patient's skin or can be applied through an interface such as patient's hair.

In another embodiment of this invention the apparatus consists of an RF source and a coupling element with the coupling element connected to the RF source through a matching network. The matching network is designed to maximize delivery of the RF energy from the RF source to the coupling element and to the tumor via evanescent waves. The matching network can consist of fixed components such as fixed capacitors and inductors, or can consists of variable components such as variable capacitors and variable inductors or a combination of fixed and variable components.

In yet another embodiment of this invention the apparatus consists of an RF source, a control network, a matching network, and a coupling element. The RF source is connected to the coupling element via wire or RF cable through the control network and the matching element. The control network consists of an amplifier, a coupler, two power sensors, and a microcontroller. The microcontroller monitors the transmitted and reflected power to/from the matching network and the coupling element. The microcontroller is capable of adjusting the power of the RF source and amplifier, and in the case that the elements in the matching network are variable, it can adjust the matching network to optimize delivery of the desired RF power to the tumor and minimize wasted RF energy. The microcontroller can also set the frequency of the RF source to a particular frequency or range of frequencies. In addition, a temperature sensor can be integrated into the coupling element to monitor the patient's skin temperature via the microcontroller and reduce the RF power level to keep the temperature below a desired level.

In another embodiment of this invention the output of an RF oscillator is divided using a three-way RF splitter and the three outputs are connected to three coupling elements through three RF switches, three phase-shifters, three control networks and three matching networks. The three control networks can each have their own microcontroller or share one microcontroller. The microcontroller(s) can switch the RF switches to turn on each coupling element independently or turn on any combination of the three coupling elements simultaneously. The three coupling elements can be used for treatment of a tumor by being positioned on the head (for example) in three perpendicular directions (or positioned to point in three different directions targeting the tumor). The microcontroller(s) can vary the phase and magnitude of the RF energy delivered to each coupling element and by turning on more than one of the coupling elements the direction and/or polarization of the evanescent waves within the tumor can be varied. The typical power that can be applied to each coupling element is limited by the local heating of the patient's skin below the coupling element. By having three coupling elements positioned on different parts of the patient's skin it is possible to deliver a higher level of RF power to the tumor without exceeding local heating limits of the patient's skin.

In a particular embodiment of this invention three RF oscillators are connected to three coupling elements through three RF switches, three phase-shifters, three control networks and three matching networks. One microcontroller is used to control all three subsystems. The microcontroller can switch the RF switches to turn on each coupling element independently or turn on any combination of the three coupling elements simultaneously. The three coupling elements can be used for treatment of a tumor by being positioned on the head (for example) in three perpendicular directions (or positioned to point in three different directions targeting the tumor). The microcontroller can vary the phase and magnitude of the RF power delivered to each coupling element and by turning on more than one of the coupling elements the direction and/or polarization of the evanescent waves within the tumor can be varied. The microcontroller can also set the frequency of the RF sources to a particular frequency or range of frequencies.

The following is a detailed explanation of the figures:

FIG. 1 is a drawing of the prior art of an apparatus for treating cancer tumors consisting of an RF source 100 connected via wires or cables 110 to two electrodes 120 for capacitively applying electric field 130 to a tumor.

Figure 2:
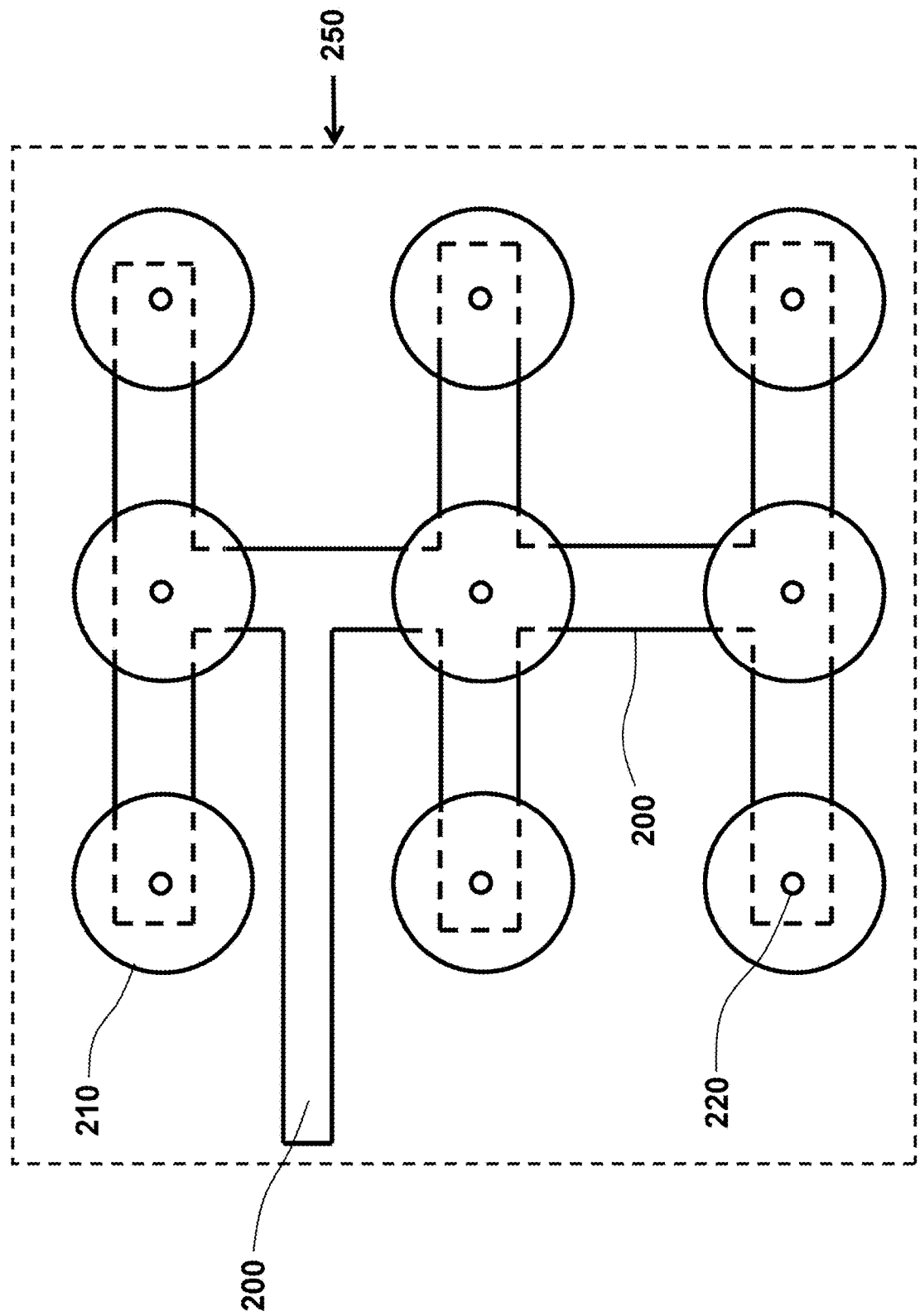
FIG. 2 is a drawing of an electrode consisting of an array of nine elements electrically connected together for capacitively applying the electric field for the apparatus in FIG. 1.

FIG. 2 is a drawing of an electrode array 250 used in prior art for capacitive coupling in conjunction with the apparatus shown in FIG. 1. The electrode array consists of nine electrode elements 210 which are made from ceramic with metal backing and are electrically connected through a flexible cable 200 connected to the back of the electrodes. The electrode elements have a temperature sensor 220 that can measure the skin temperature.

Figure 3A:
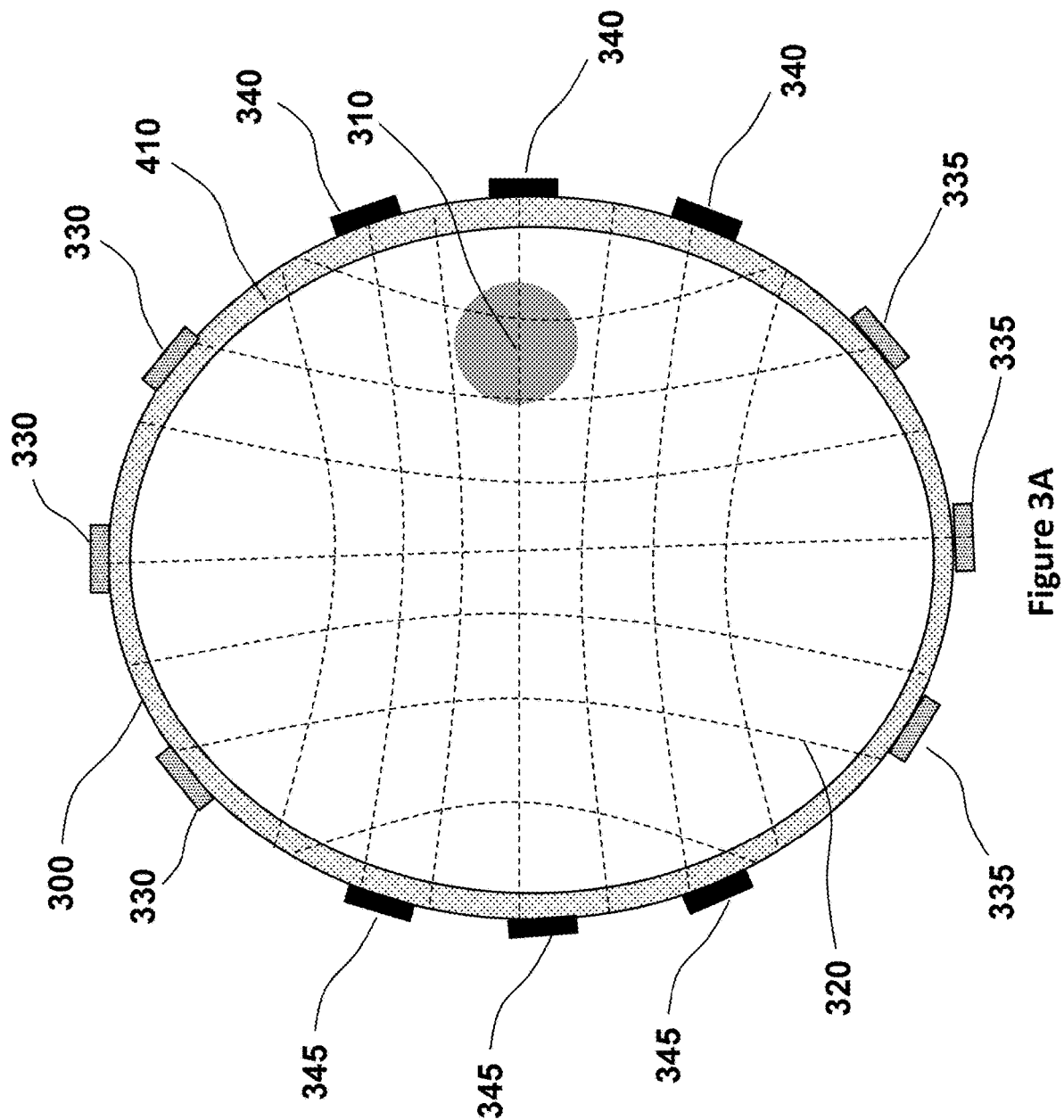
FIG. 3A is a drawing of cross-section of a head showing two sets of electrodes capacitively applying electric fields in two different directions to a tumor in the brain.

FIG. 3A is a drawing of cross section of a head 300 showing two sets of electrode arrays 330 & 335, and 340 & 345, used with the apparatus in prior art shown in FIG. 1 to capacitively apply electric fields 320 in two different directions to a tumor 310 in the brain. The electrode sets 330, 335, 340, and 345 shown are cross section of the nine element array electrodes similar to the electrode array 250 shown in FIG. 2. In this case to capacitively apply electric field to a head a total of 36 electrodes are used.

Figure 3B:
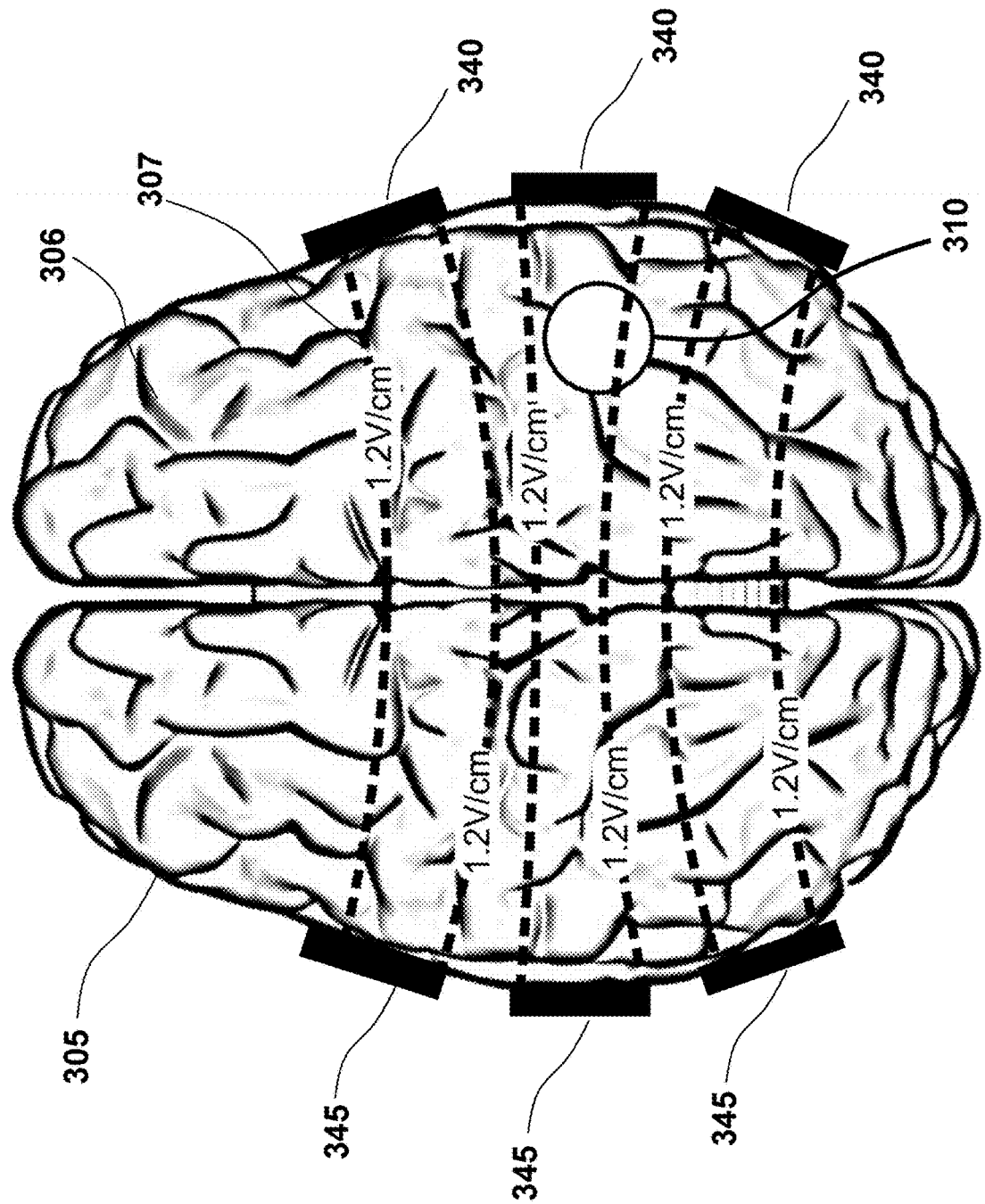
FIG. 3B is a drawing of cross-section of a head showing one of set of electrodes capacitively applying electric fields to a tumor in the brain and the electric field contours in the brain and the tumor.

FIG. 3B is a drawing of cross-section of a head 305 showing one of the set of electrodes 340 and 345 used to capacitively apply electric fields to a tumor 310 in the brain 306 and the electric field contours 307 in the brain and the tumor. Approximately 30 Watt of power is delivered across the electrodes resulting in an electric field with an average of around 1.2 V/cm in the brain and the tumor. In this case, the electrical conductivity of the brain is assumed to be uniform.

Figure 4:
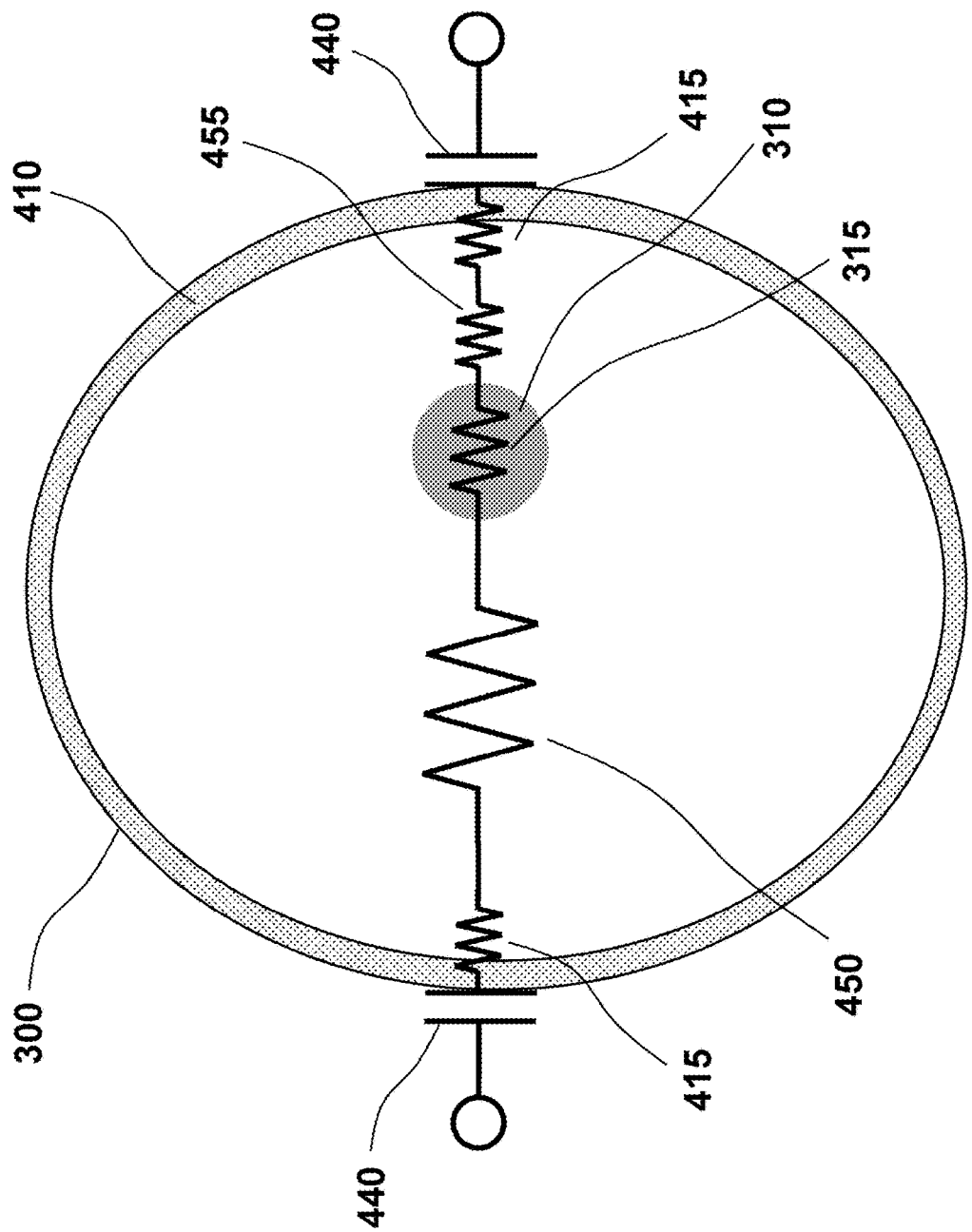
FIG. 4 is a simplified equivalent circuit schematic showing the various parts of the head and brain in the case when electric field is applied capacitively to the head as in FIG. 3A.

FIG. 4 is a simplified equivalent circuit schematic showing the various parts of the head and brain in the case when electric field is applied capacitively to the head 300 as in FIG. 3A for the prior art. The schematic consists of capacitors associated with the electrodes 440 at the interface with the skin followed by two resistors 415 associated with the skin 410. Then there are resistors 450 and 455 associated with the tissue between the skin layer and the tumor 310 which is represented by resistor 315.

Figure 5A:
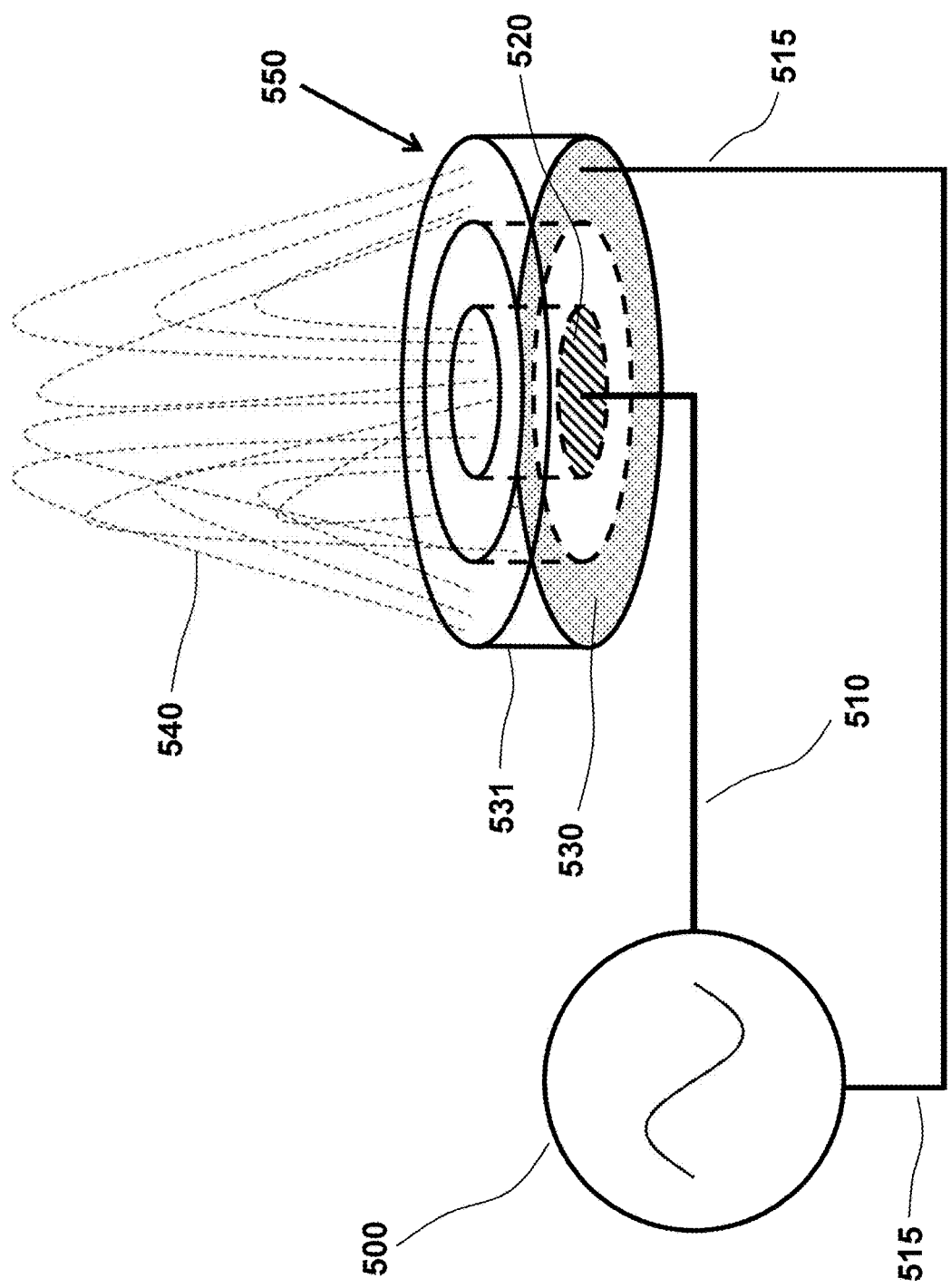
FIG. 5A is a drawing of one embodiment of this invention illustrating an apparatus for treating cancer tumors consisting of an RF source connected to a coupling element for launching evanescent waves into tumors.

FIG. 5A is a drawing of one embodiment of this invention illustrating an apparatus for treating cancer tumors consisting of an RF source 500 which can be an oscillator or a signal source with an output frequency range between 10 kHz to 500 kHz. Depending on the cancer cell type, the oscillator is set to a particular frequency (or frequencies) that maximizes killing of cancer cells. The output of the RF source is connected using electrically conducting wires 510 and 515 to a coupling element 550 for launching evanescent waves 540 into tumors. The evanescent waves consist of a plurality of different electric field polarizations within the spatial volume around the coupling element. The coupling element 550 in this embodiment is an open-ended coaxial waveguide antenna which has an electrical configuration consisting of two concentric circles 520 and 530 with the inner circle 520 connected to the RF source through cable 510 and the outer circle/ring 530 connected to the RF source through cable 515. The circles are made from an electrically conductive material such as metal or from an insulator that is covered with an electrically conductive layer. The electrically conductive rings are supported or attached to a non-conductive substrate 531. Even though the figure shows the evanescent waves 540 emanating from top of the coupling element, for this design, the evanescent waves emanate both from top and bottom of the coupling element.

Figure 5B:
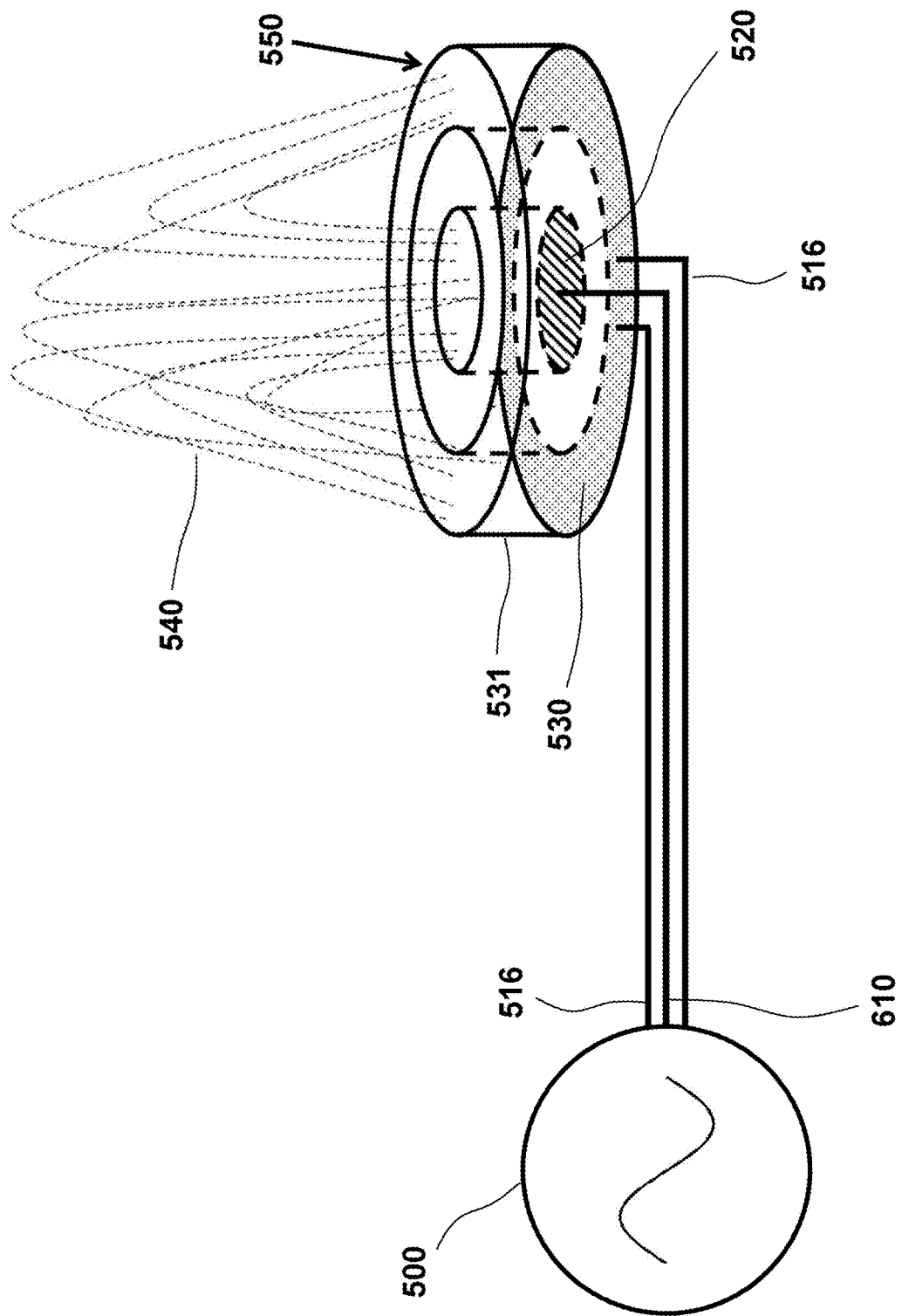
FIG. 5B is a drawing of another embodiment of this invention illustrating an apparatus for treating cancer tumors consisting of an RF source connected using a coaxial cable to a coupling element for launching evanescent waves into tumors.

FIG. 5B is a drawing of another embodiment of this invention illustrating an apparatus for treating cancer tumors. This embodiment is similar to the embodiment shown in FIG. 5A except that a coaxial cable connects the RF source 500 to the coupling element 550 which in this case is an open-ended coaxial waveguide antenna. The coaxial cable comprises of a center conductor 610 connected to the center circle 520 of the coupling element and an outer conductor 516 connected to the outer circle/ring of the coupling element.

Figure 5C:
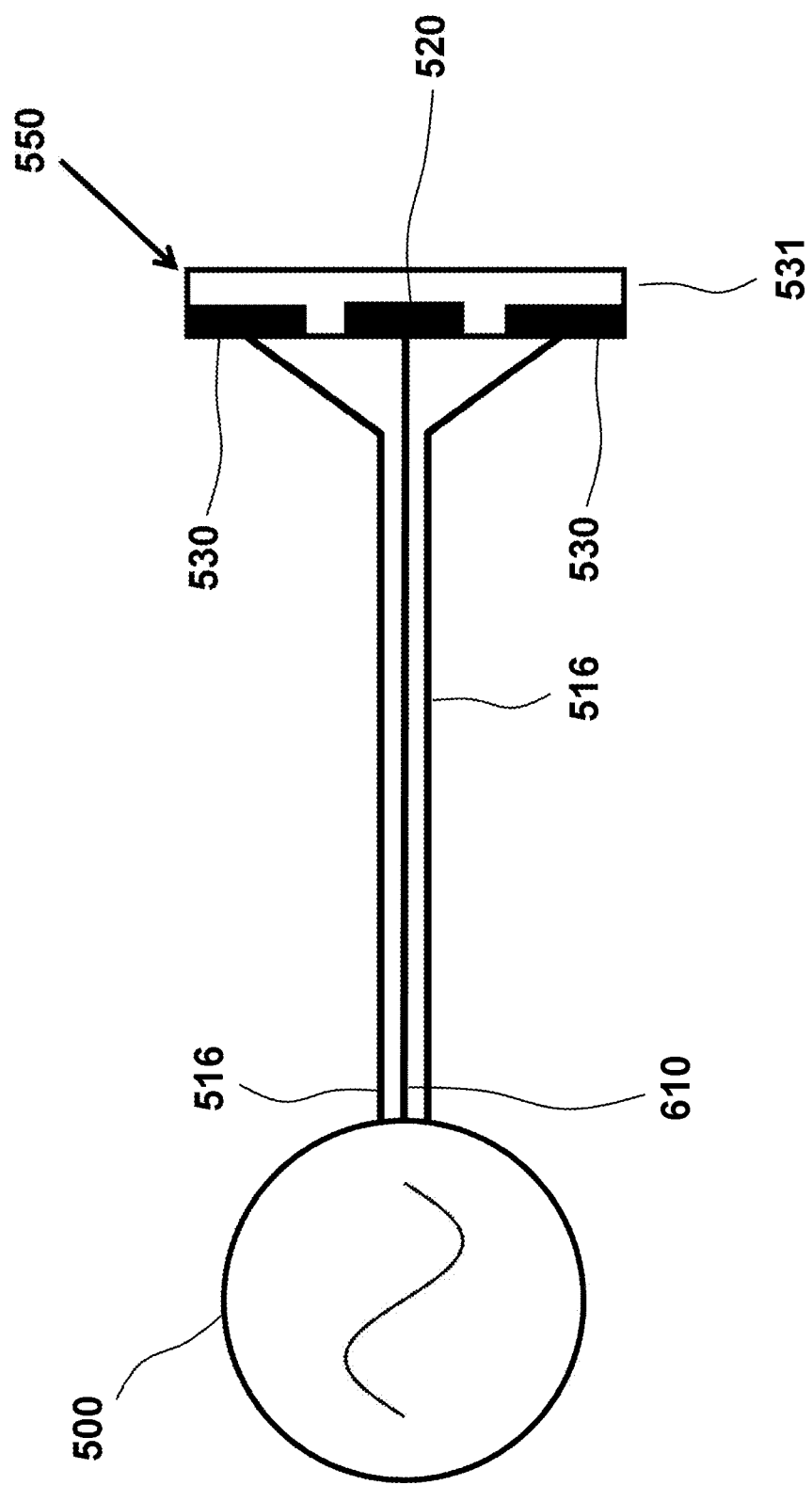
FIG. 5C is a drawing showing the same embodiment as FIG. 5B with the side view of the coupling element.

FIG. 5C is a drawing showing the same embodiment as FIG. 5B with the side view of the coupling element 550. The center conductor 610 of the coaxial cable is connected to the center conductor 520 of the coupling element and the outer conductor 516 of the coaxial cable is connected to the outer conductor 530 of the coupling element. The conductors of the coupling element are made from a metal such as aluminum, copper, silver, or gold attached to a non-conductive substrate such as Mylar, plastic, FR-4, or alumina. The non-conductive substrate can also be made from a fabric such as cotton, polyester, Lycra or other similar fabrics.

FIG. 6A is a drawing of another embodiment of this invention. This embodiment is similar to the embodiment in FIG. 5A except a matching element 650 is inserted between the RF source 500 and the coupling element 550 in order to maximize delivery of power to the tumor via evanescent waves 540.

Figure 6B:
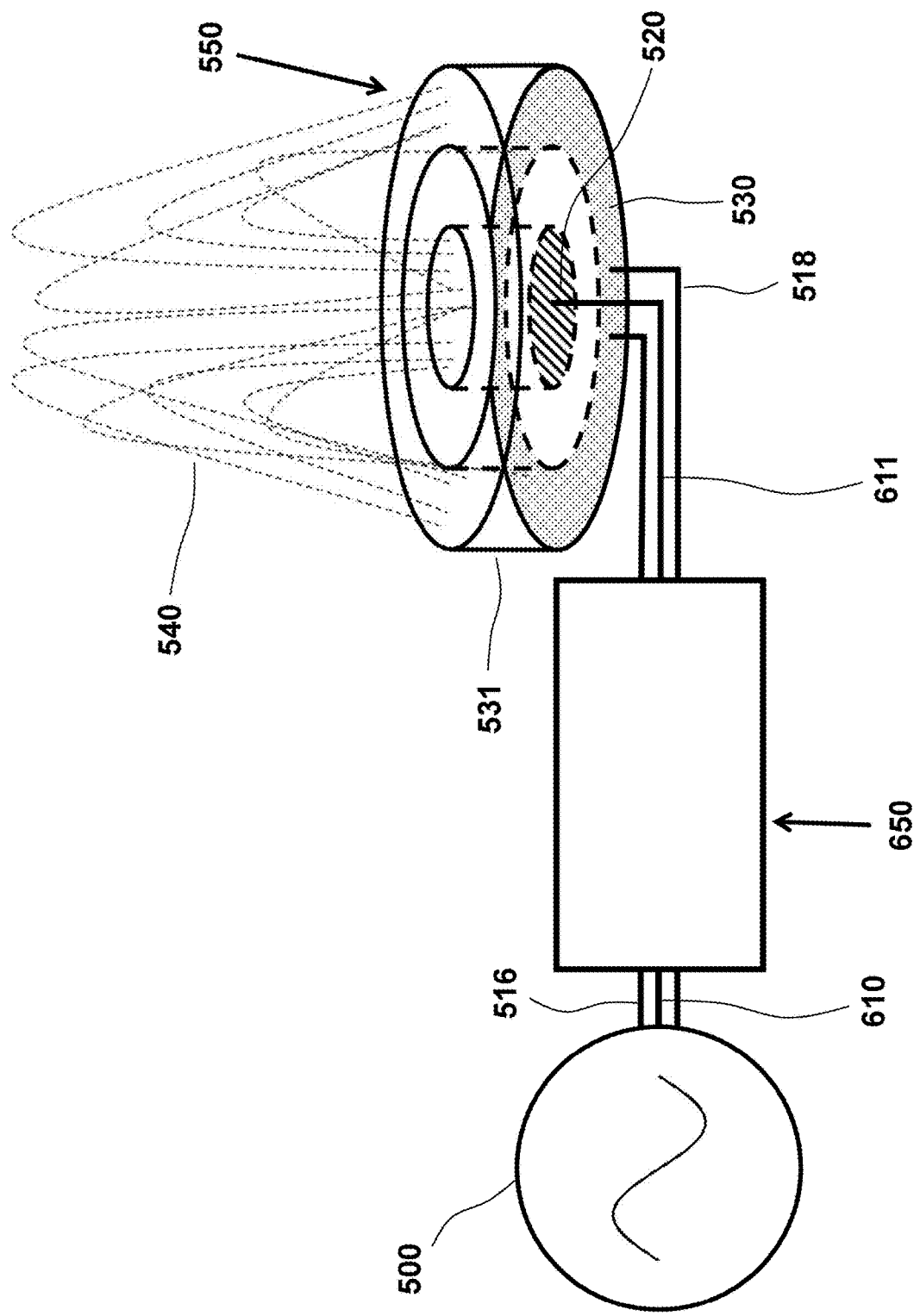
FIG. 6B is a drawing of another embodiment of this invention. This embodiment is similar to the embodiment in FIG. 5B except a matching element or coupling device is inserted between the RF source and the coupling element in order to maximize coupling of the evanescent waves to the tumor.

FIG. 6B is a drawing of another embodiment of this invention. This embodiment is similar to the embodiment in FIG. 5B except a matching element 650 is inserted between the RF source 500 and the coupling element 550 in order to maximize power delivery to the tumor via evanescent waves 540. A coaxial cable with center conductor 610 and outer conductor 516 connects the RF source to the matching element 650. The output of the matching element is connected to the coupling element using a coaxial cable with the center conductor 611 and outer conductor 518.

Figure 7:
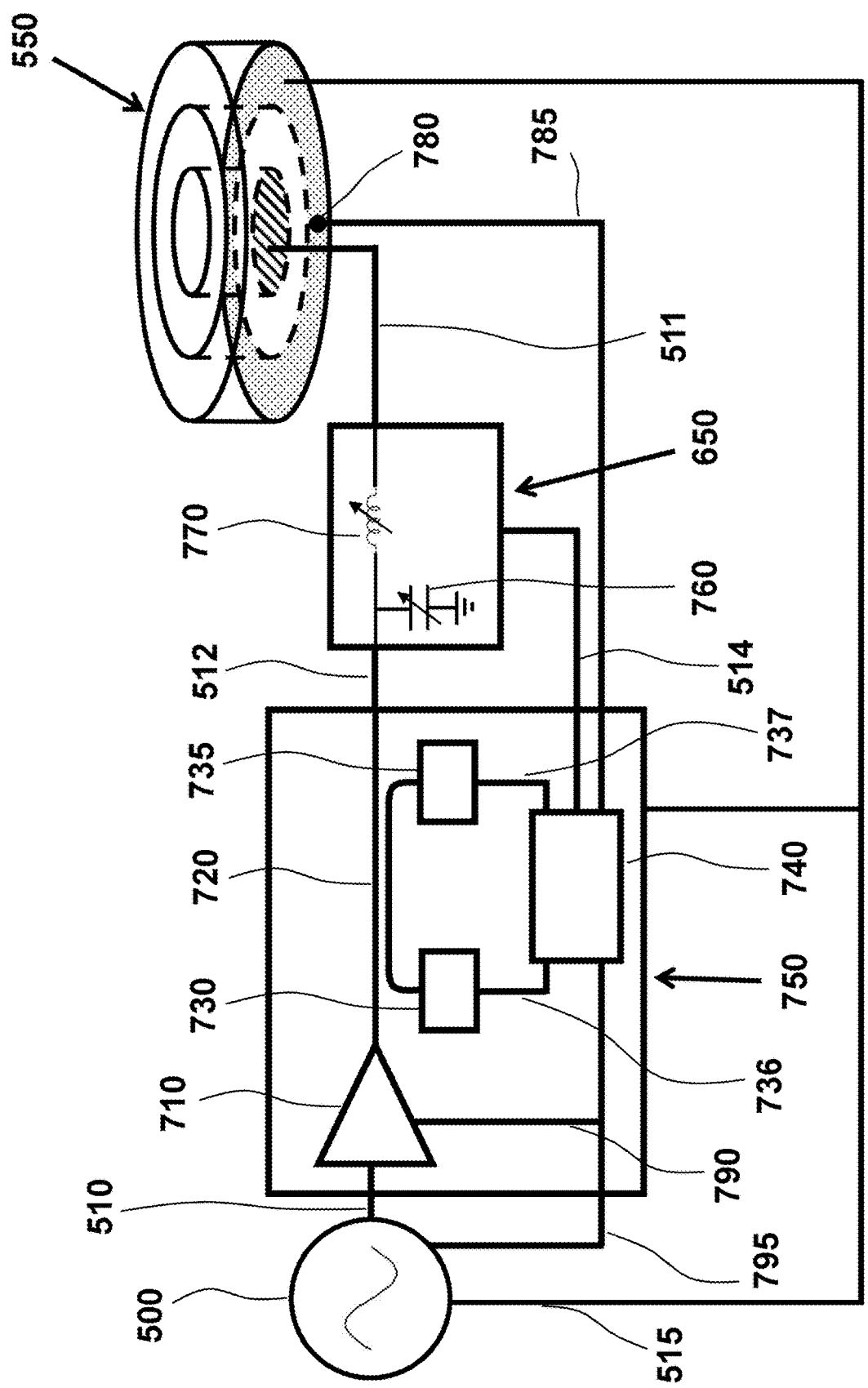
FIG. 7 is a drawing of another embodiment of this invention. This embodiment is similar to the embodiment in FIG. 6A except an amplifier as well as control circuits, including a microcontroller, have been added between the RF source and the matching element.

FIG. 7 is a drawing of another embodiment of this invention. This embodiment is similar to the embodiment in FIG. 6A except a control module 750 is inserted between the RF source 500 and the matching element 650. The control module 750 consists of an RF amplifier 710, a coupler 720, two RF sensors 730 and 735, and a microcontroller 740. The matching element in this embodiment consists of a variable capacitor 760 and a variable inductor 770. The output of the RF source is connected to the input of the amplifier using a cable/wire 510 and the output of the coupler is connected to the input of the matching element using a cable/wire 512. The output of the matching element is connected to the coupling element 550 using cable/wire 511. A temperature sensor 780 which will be capable to measure the skin temperature of the patient is attached to the coupling element and is connected to the microcontroller using wire 785. The RF source, RF amplifier, two RF sensors and the matching element, are also connected to the microcontroller using cables/wires 795, 790, 736, 737, and 514 respectively. The microcontroller can monitor the reflected and transmitted power using the RF sensors and the coupler and control the frequency and power output of the RF source, the gain of the RF amplifier, and vary the parameters of the matching element to maximize transfer of power to the coupling element and the tumor. Instead of RF sensors one can also use voltage and current sensors to monitor the RF power from the RF source. The microcontroller can also monitor the skin temperature and reduce RF power to keep the skin temperature below the maximum target temperature for the comfort of the patient.

Figure 8A:
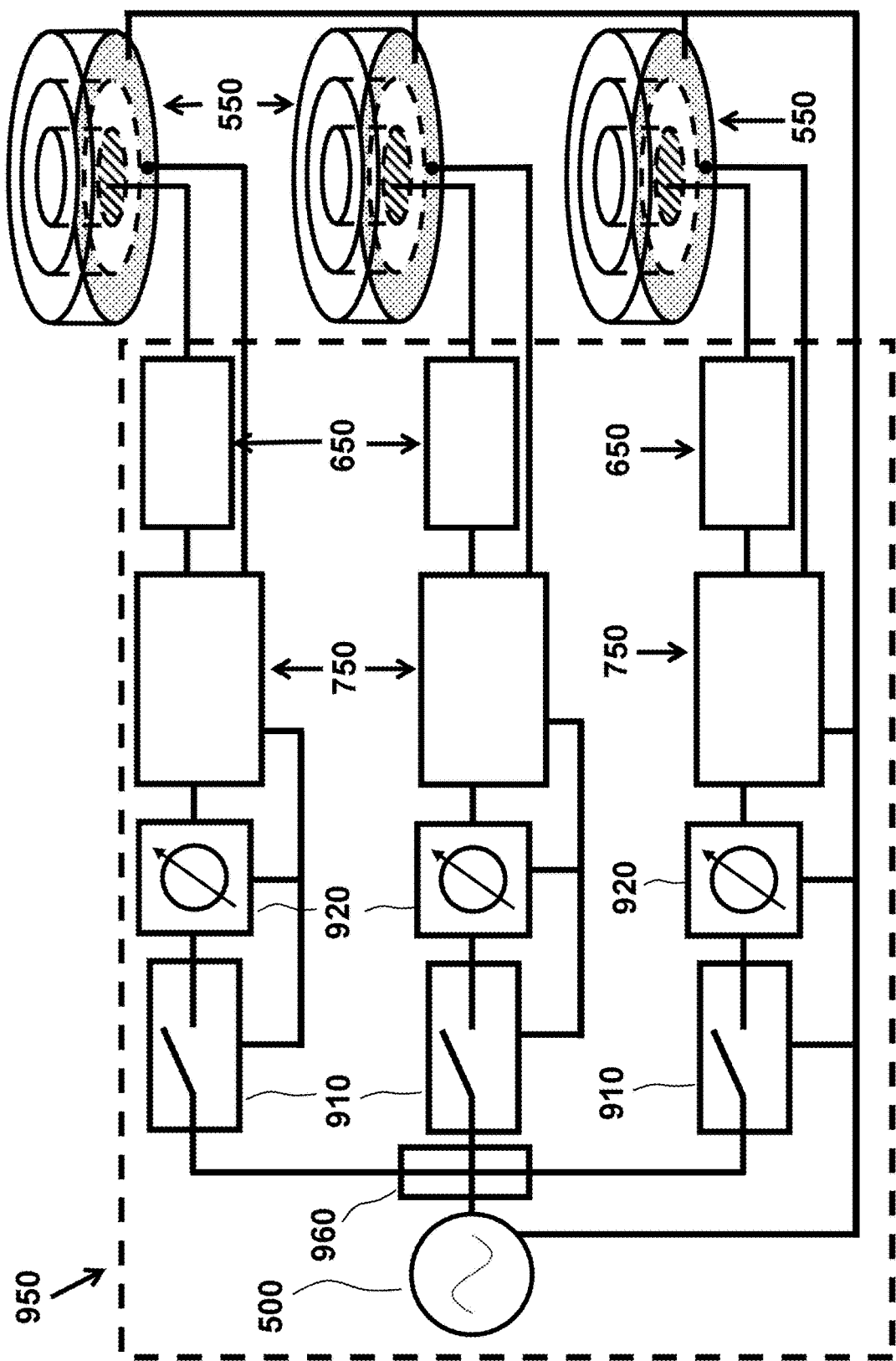
FIG. 8A is a drawing of another embodiment of this invention. In this embodiment three of the embodiments shown in FIG. 7 are used with the RF source split by a three-way splitter and is connected through three switches and phase-shifters to each coupling element that launches evanescent waves. Each coupling element can be turned on independently or in conjunction with another coupling element (or elements).

FIG. 8A is a drawing of another embodiment 950 of this invention. In this embodiment three of the embodiments shown in FIG. 7 are used with the RF source 500 with its output split by a three-way splitter 960. The three outputs from the three-way splitter are connected through three RF switches 910 and three phase-shifters 920 to the input of the three control modules 750. As in FIG. 7 three matching elements 650 are between the control module and the coupling elements 550. The microcontroller inside the control module can control each RF switch and phase-shifter independently allowing it to control the RF power delivered to each coupling element. By controlling the three RF switches, the microcontroller can turn-on the RF power to each coupling element one at a time or simultaneously to two coupling elements, or to all three coupling elements at the same time. In addition, by controlling the three phase-shifters the phase of the RF power delivered to the coupling element can be varied. By controlling the number of coupling elements that are turned-on (RF power is applied to), the phase of the RF power, the duration each of them is turned on, and the magnitude of the RF power (by controlling amplifier 710 in FIG. 7, or the RF source 500), the strength and plurality of different electric field polarizations within the evanescent waves can be varied to optimize the treatment of the tumor. As mentioned previously, the microcontroller can also vary the frequency of the RF source and the value of the matching elements to optimize delivery of evanescent waves to the tumor.

Figure 8B:
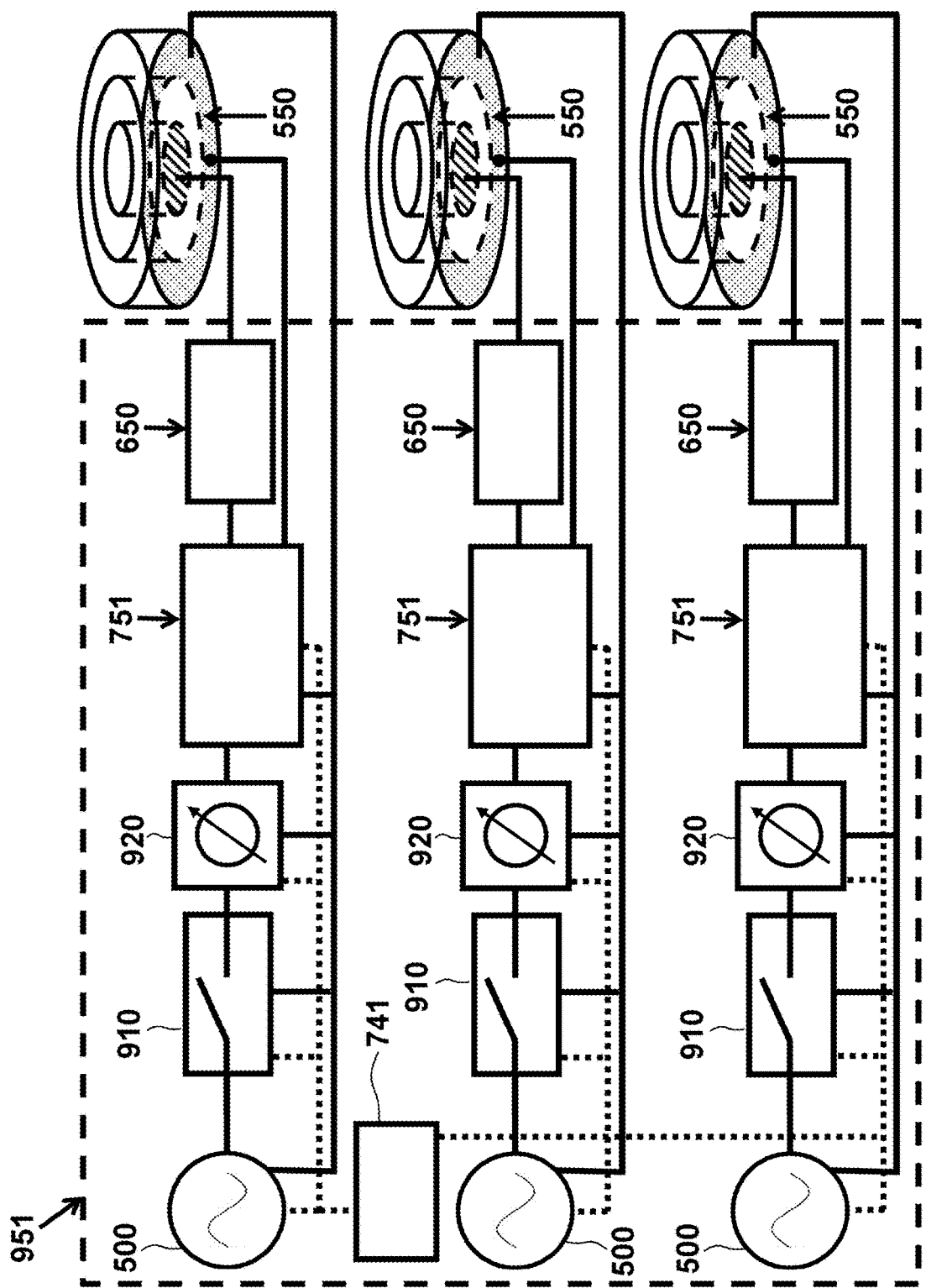
FIG. 8B is a drawing of another embodiment of this invention. This embodiment is similar to the embodiment shown in FIG. 8A except that three separate oscillators along with three separate switches, phase-shifters, amplifiers and matching elements are used to provide RF power to three coupling elements. A microcontroller controls and monitors the RF power provided to each coupling element and can turn on each coupling element independently or in conjunction with another coupling element (or elements).

FIG. 8B is a drawing of another embodiment 951 of this invention. This embodiment is similar to the embodiment shown in FIG. 8A except that three separate RF oscillators 500 along with three separate switches 910, phase-shifters 920, amplifiers 751 and matching elements 650 are used to provide RF power to three coupling elements 550. A microcontroller 741 controls the RF oscillators, switches, phase-shifter, and amplifiers as well as monitors the RF power provided to each coupling element either by measuring the power using power sensors or combination of voltage and current sensors. The microcontroller can turn on each coupling element independently or in conjunction with another coupling element (or elements). In addition, by controlling the three phase-shifters the phase of the RF power delivered to the coupling element can be varied. By controlling the number of coupling elements that are turned-on, the duration each of them is turned on, the phase of the RF power, and the magnitude of the RF power, the strength and plurality of different electric field polarizations within the evanescent waves can be varied to optimize the treatment of the tumor.

Figure 9A:
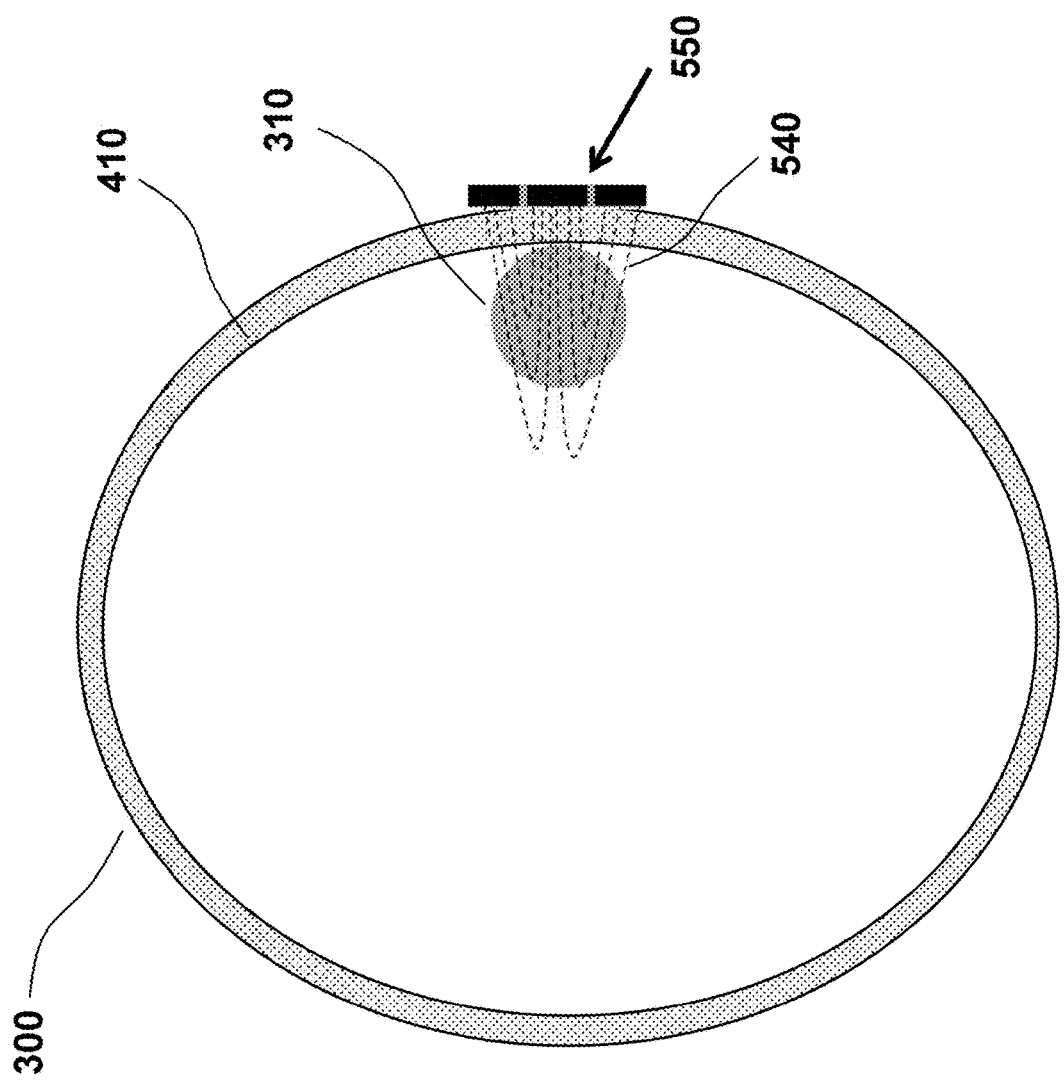
FIG. 9A is a drawing of cross-section of a head showing the coupling element in FIG. 7 launching evanescent waves into a tumor.

FIG. 9A is a drawing of cross-section of a head 300 with skin layer 410 showing the coupling element 550 from the apparatus in FIG. 7 launching evanescent waves 540 with plurality of different electric field polarizations into a tumor 310.

Figure 9B:
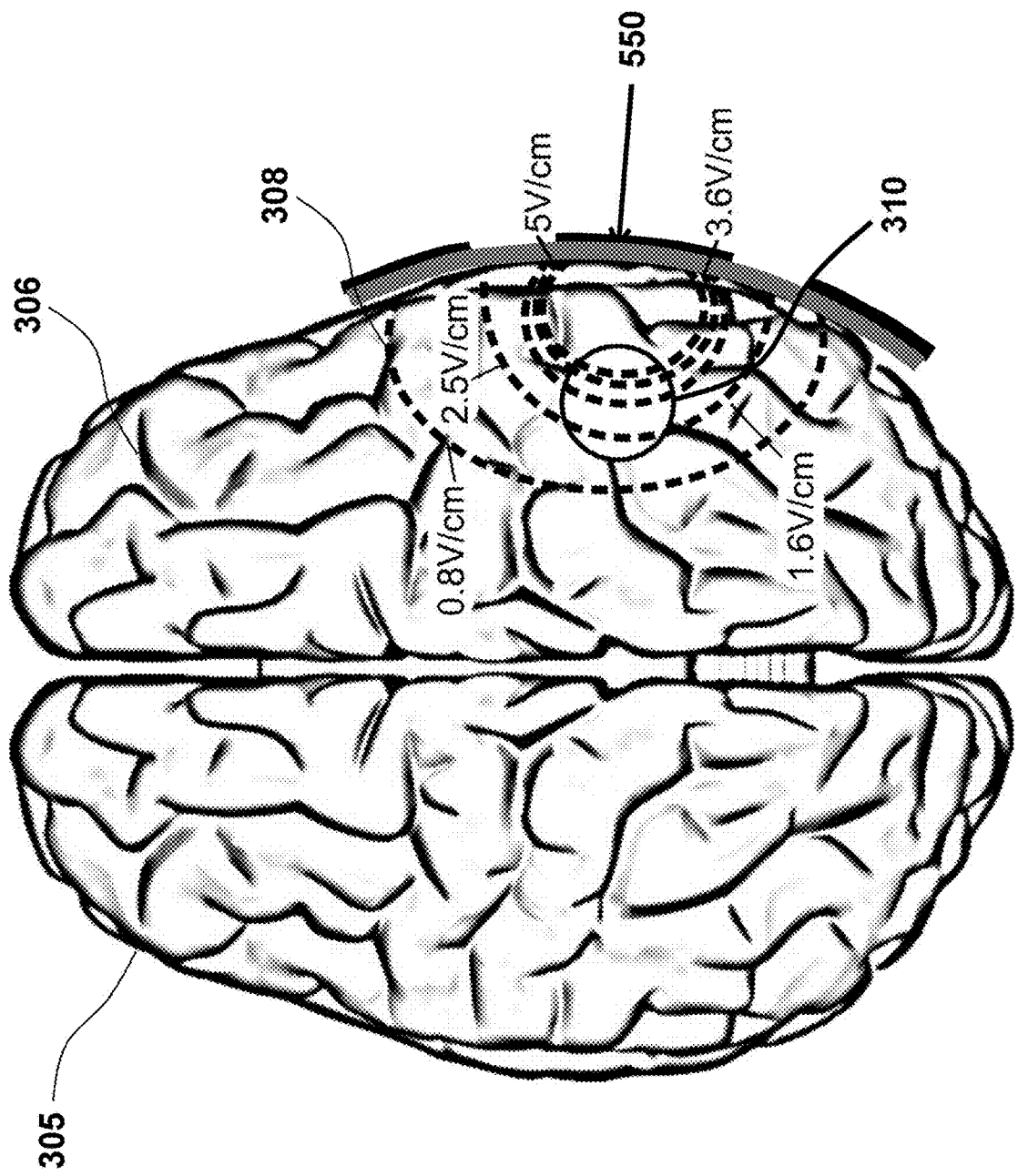
FIG. 9B is a drawing of cross-section of a head showing the coupling element in FIG. 7 launching evanescent waves into a tumor in the brain and the electric field contours in the brain and the tumor.

FIG. 9B is a drawing of cross-section of a head 305 showing the coupling element 550 from the apparatus in FIG. 7 launching evanescent waves into a tumor 310 in the brain 306 and the electric field contours 308 with plurality of different electric field polarizations in the brain and the tumor. Approximately 10 Watt of RF power is applied to the coupling element resulting in electric field contours of varying strength concentrated around and in the tumor with an average electric field of 3 V/cm. In this case, the electrical conductivity of the brain is assumed to be uniform. Lower power level of 10 Watt is used compared to 30 Watt in FIG. 3B and although the electric fields are low through parts of the brain, they are higher in the tumor compared to FIG. 3B resulting in higher efficacy in killing cancer cells.

Figure 10:
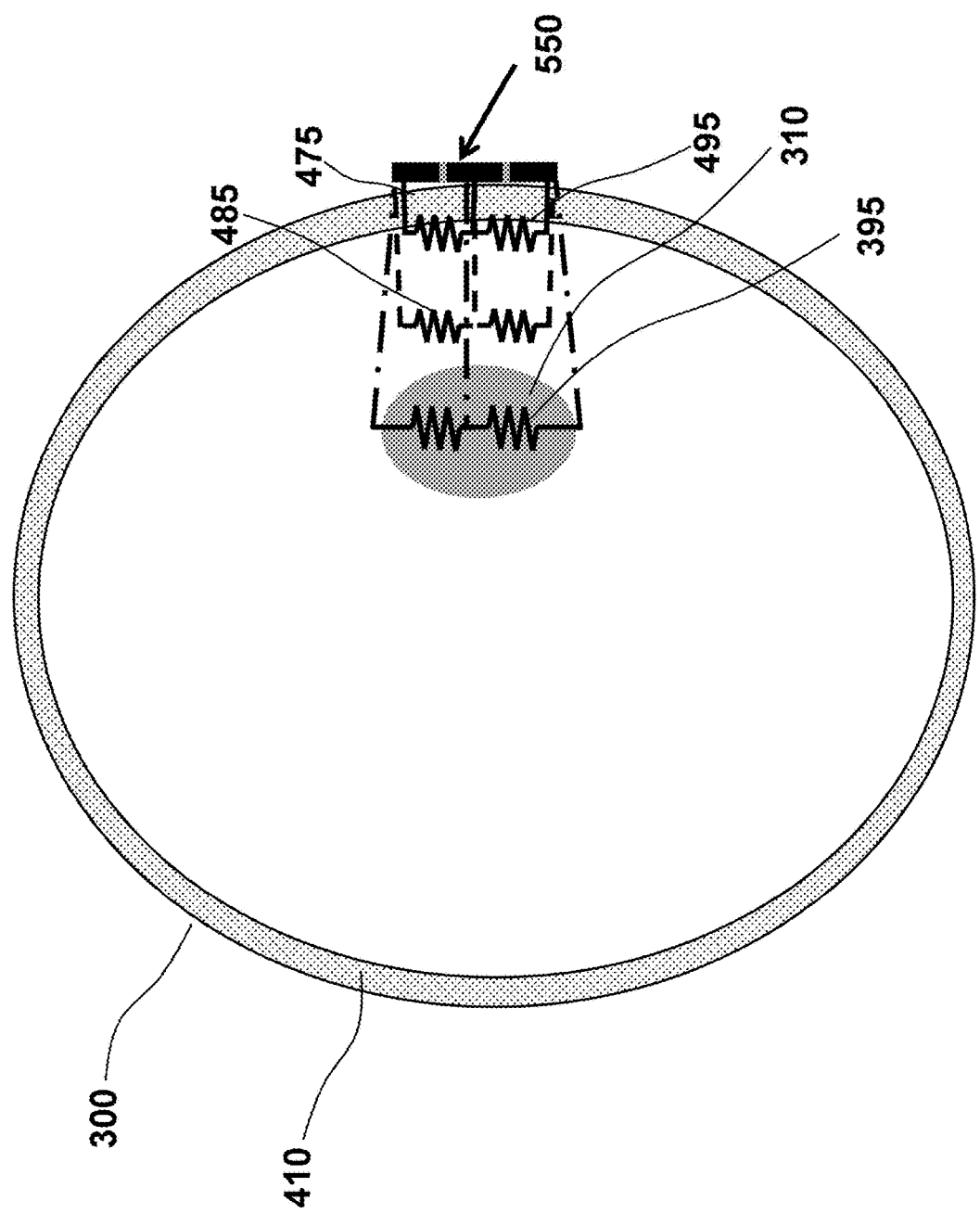
FIG. 10 is a simplified equivalent circuit schematic showing the various parts of the head and brain in the case when evanescent waves are coupled to the head as in FIG. 9A.

FIG. 10 is a simplified equivalent circuit schematic showing the various parts of the head and brain in the case when evanescent waves are coupled to a tumor in the head 300 as in FIG. 9A. The schematic consists of coupling element 550 followed by capacitor 475 and resistor 495 associated with the skin 410. The resistor 485 is associated with the tissue between the skin layer and the tumor 310 which is represented by resistor 395. The equivalent circuit model with the coupling element is represented with several parallel circuits compared to the components that were in series in the case of capacitive coupling shown in FIG. 4.

Figure 11:
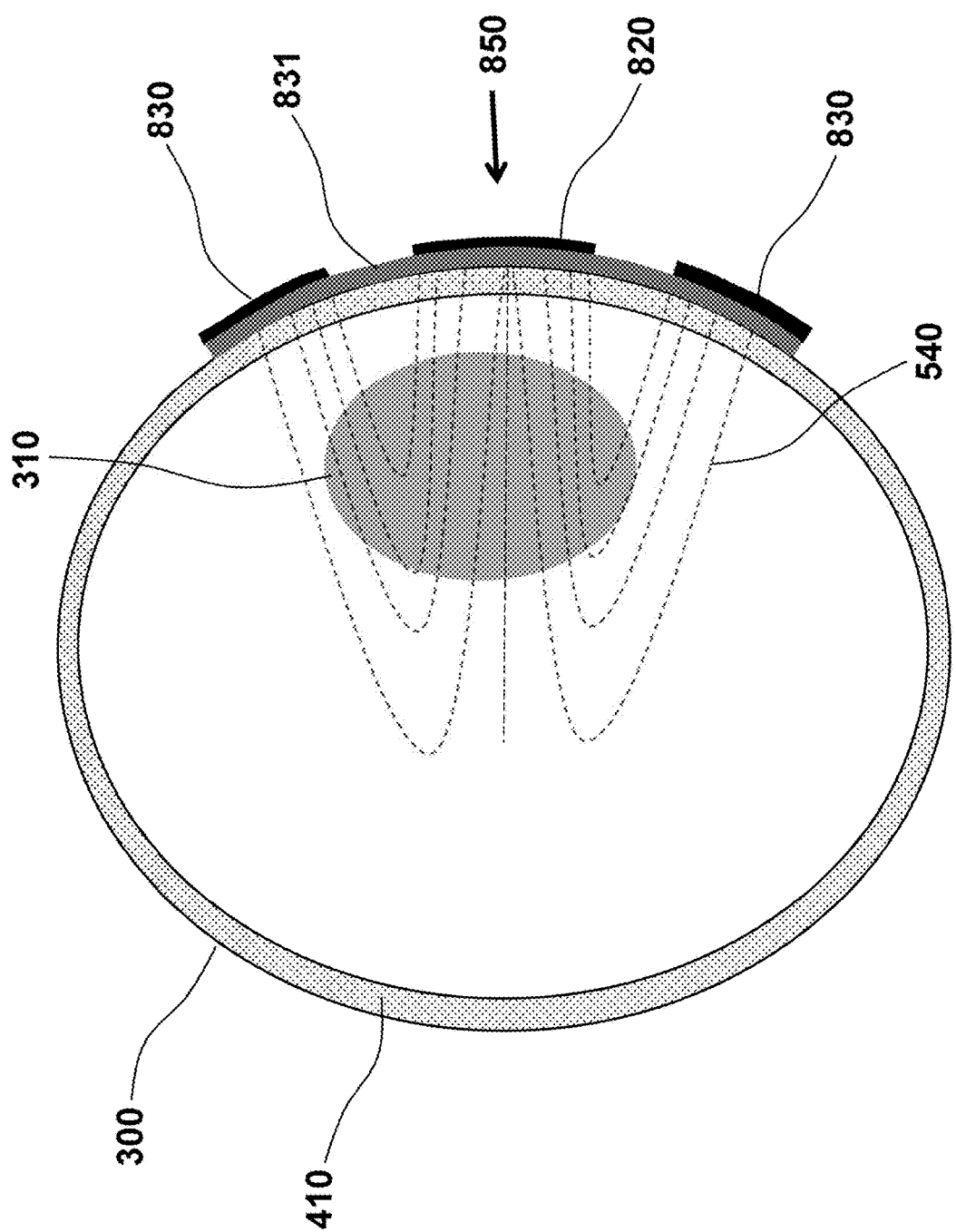
FIG. 11 is a drawing of cross-section of a head showing another type of coupling element launching evanescent waves into a tumor.

FIG. 11 is a drawing of cross-section of a head 300 with skin layer 410 showing another type of coupling element 850 launching evanescent waves 540 with plurality of different electric field polarizations into a tumor 310. The coupling element consists of a center conductor 820 with an outer conductor 830 is made on a flexible non-conductive substrate 831.

Figure 12:
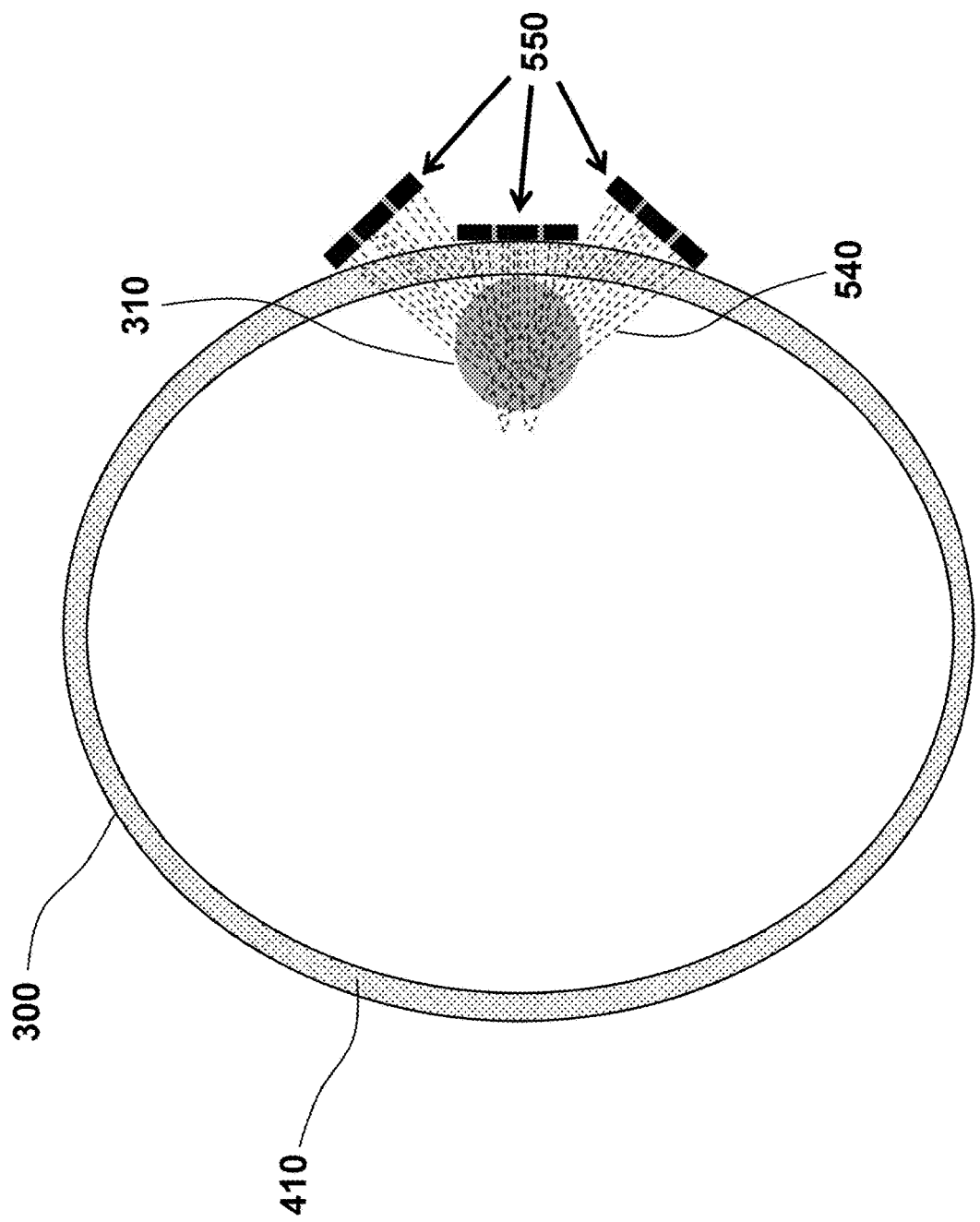
FIG. 12 is a drawing of cross-section of a head showing the three coupling elements in FIG. 8B launching evanescent waves into a tumor at different angles.

FIG. 12 is a drawing of cross-section of a head 300 with skin layer 410 showing the three coupling elements 550 from FIG. 8B launching evanescent waves 540 with plurality of different electric field polarizations into a tumor 310 at different angles. Each of the three coupling elements can be turned-on independently or in conjunction, to change the direction of the combined beam and distribution of electric field polarizations for optimum treatment of the tumor.

Figure 13:
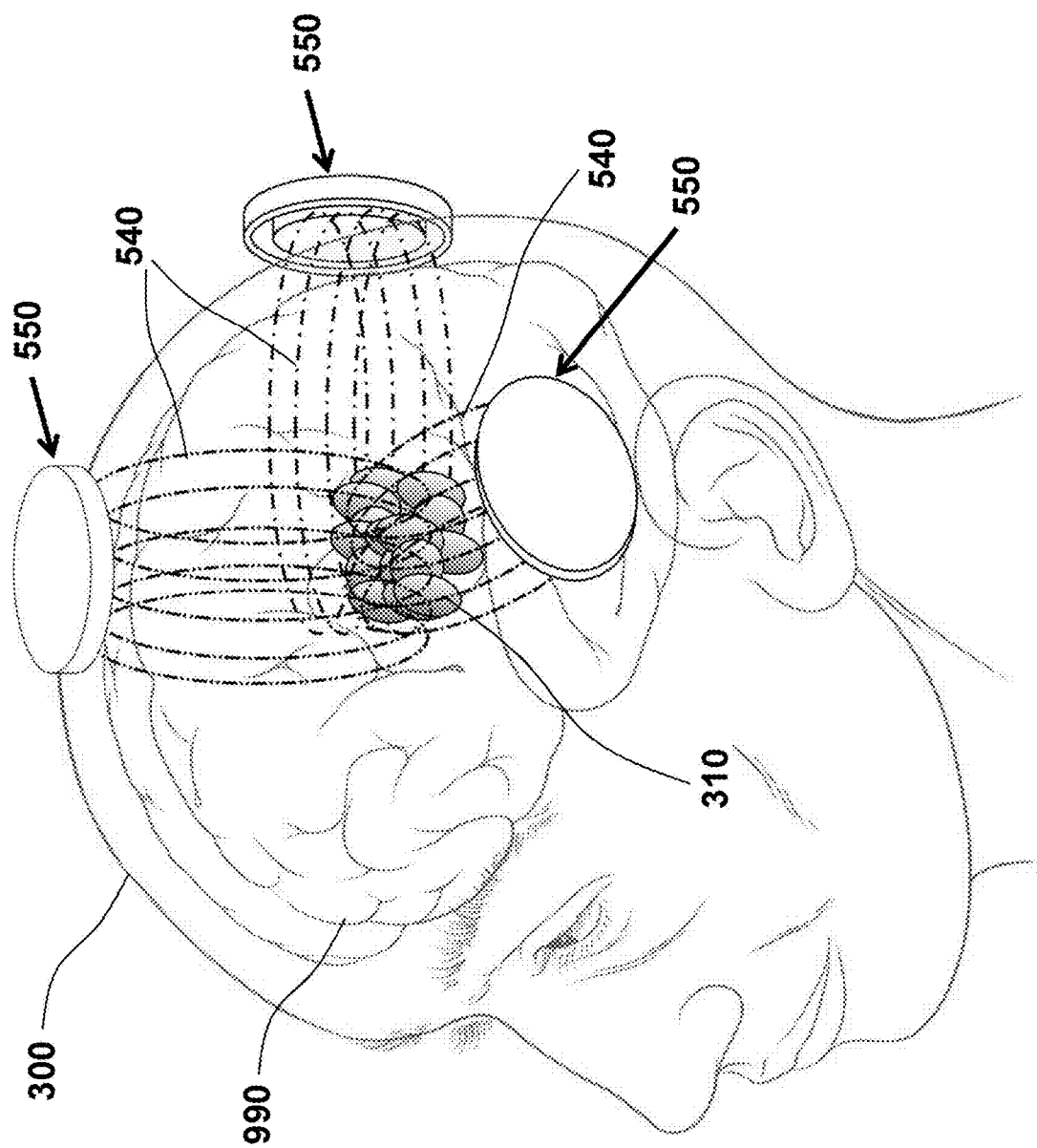
FIG. 13 is a drawing of a head showing the three coupling elements in FIG. 8B launching evanescent waves into a tumor in the brain. The three coupling elements are launching the evanescent waves perpendicular to each other.

FIG. 13 is a drawing of a head 300 showing the three coupling elements 550 from FIG. 8B launching evanescent waves 540 with plurality of different electric field polarizations into a tumor 310 in the brain 990 at different angles. In this case the three coupling elements are in perpendicular direction to each other and by turning on each coupling element individually or in conjunction, and by varying the amplitude and/or phase of the RF signal to each element the direction and concentration of the evanescent waves and distribution of electric field polarizations can be varied to optimize the treatment of the tumor.

FIG. 14A is a drawing of the cross section of a coupling element, for launching evanescent waves with plurality of different electric field polarizations within a spatial region, that is an open-ended coaxial waveguide antenna consisting of a center conductor 520 and an outside conductor 530 separated from the center conductor by a dielectric layer 531.

FIG. 14B is a drawing similar to FIG. 14A except the cross section of the coupling element is oval and it consists of a center conductor 521 and an outside conductor 541 separated from the center conductor by a dielectric layer 576.

FIG. 14C is a drawing similar to FIG. 14A except the cross section of the coupling element is square and it consists of a center conductor 522 and an outside conductor 532 separated from the center conductor by a dielectric layer 577.

FIG. 14D is a drawing similar to FIG. 14C except the corners of the square cross section are rounded and it consists of a center conductor 523 and an outside conductor 533 separated from the center conductor by a dielectric layer 578.

Figure 15A:
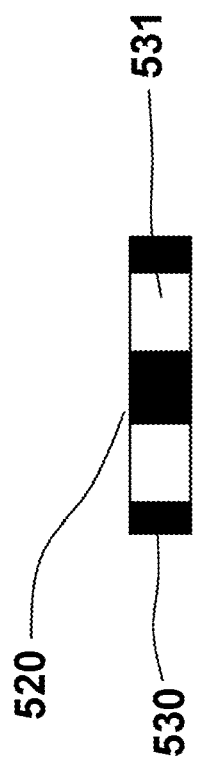
FIG. 15A is a drawing showing the side view of the coupling element shown in FIG. 14A.

FIG. 15A is a drawing of the cross-section of FIG. 14A coaxial coupling element showing the side view of the coupling element including the center conductor 520, the outside conductor 530, and the dielectric (or non-conductive) layer 531 between the center conductor and the outside conductor.

Figure 15B:
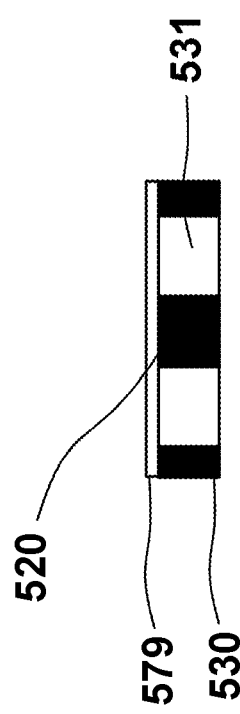
FIG. 15B is a drawing similar to the side view of the coaxial coupling element shown in FIG. 15A with an added non-conductive layer.

FIG. 15B is a drawing similar to the side view of the coaxial coupling element shown in FIG. 15A with an added non-conductive layer 579 covering the coaxial coupling element. This non-conductive layer can be added to the coupling element to prevent the surface conductivity of a patient's skin from "shorting" the coupling element when it comes in contact with the skin.

Figure 15C:
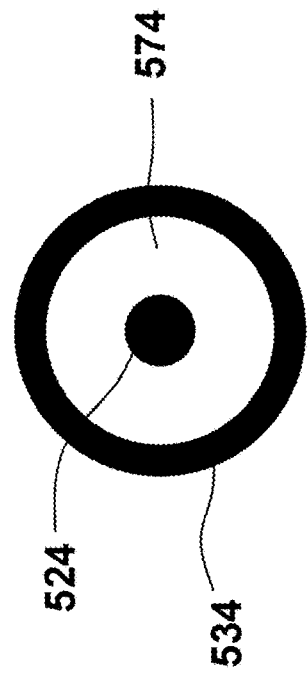
FIG. 15C and FIG. 15D are drawings of the top and side view of a different coaxial coupling element than the one shown in FIG. 14A.
Figure 15D:
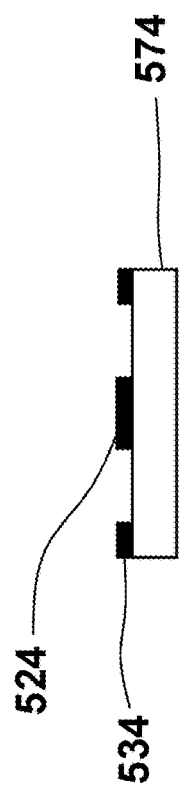

FIG. 15C and FIG. 15D are drawings of the top and side views of a different coaxial coupling element than the one shown in FIG. 14A. It consists of a center conductor 524 and outside conductor 534 and the dielectric (non-conductive) layer 574. In this case as the side view shows the conductors are on the surface of the dielectric (non-conductive) layer.

Figure 15E:
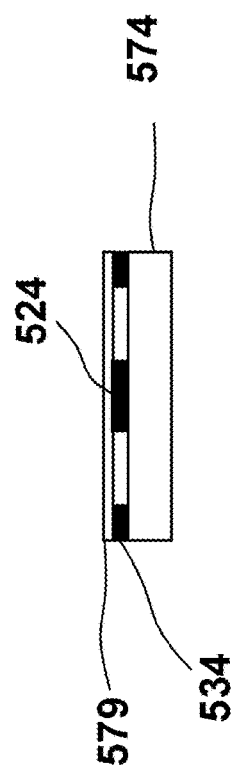
FIG. 15E is a drawing similar to the side view of the coaxial coupling element shown in FIG. 15D with an added non-conductive layer.

FIG. 15E is a drawing similar to the side view of the coaxial coupling element shown in FIG. 15D with an added non-conductive layer 579 covering the conductors of the coaxial coupling element. This non-conductive layer can be added to the coupling element to prevent the surface conductivity of a patient's skin from "shorting" the coupling element when it comes in contact with the skin. Alternatively, the dielectric (or non-conductive) side of the coupling element can be used to make contact with the patient's skin.

FIG. 16A is a drawing of a different coupling element than the one shown in FIG. 14B. The coupling element consists of two center conductors 620 and 621 and one oval shaped outside conductor 622. This coupling element can be used to target a larger tumor or to deliver higher RF power density.

FIG. 16B is a drawing of a different coupling element consisting of two coupling elements similar to the coaxial coupling element shown in FIG. 15C. The coupling element has two center conductors 623 and 624, and a shared outside conductor 625. This coupling element can be used to target a larger tumor or to deliver higher RF power density.

FIG. 16C is a drawing of a different coupling element consisting of three coupling elements similar to the coaxial coupling element shown in FIG. 15C. The coupling element has three center conductors, 626, 627, and 628, and a shared outside conductor 629. This coupling element can be used to target a larger tumor or to deliver higher RF power density.

Figure 17B:
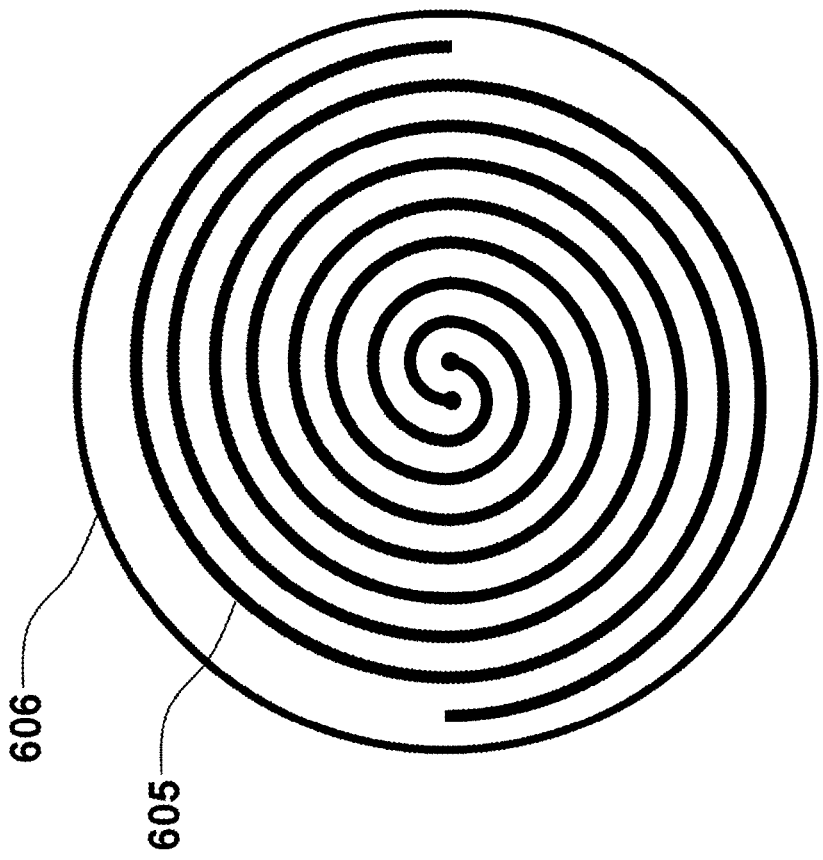
FIG. 17B is a drawing of another embodiment of a coupling element in the form of double spiral antenna.
Figure 17A:
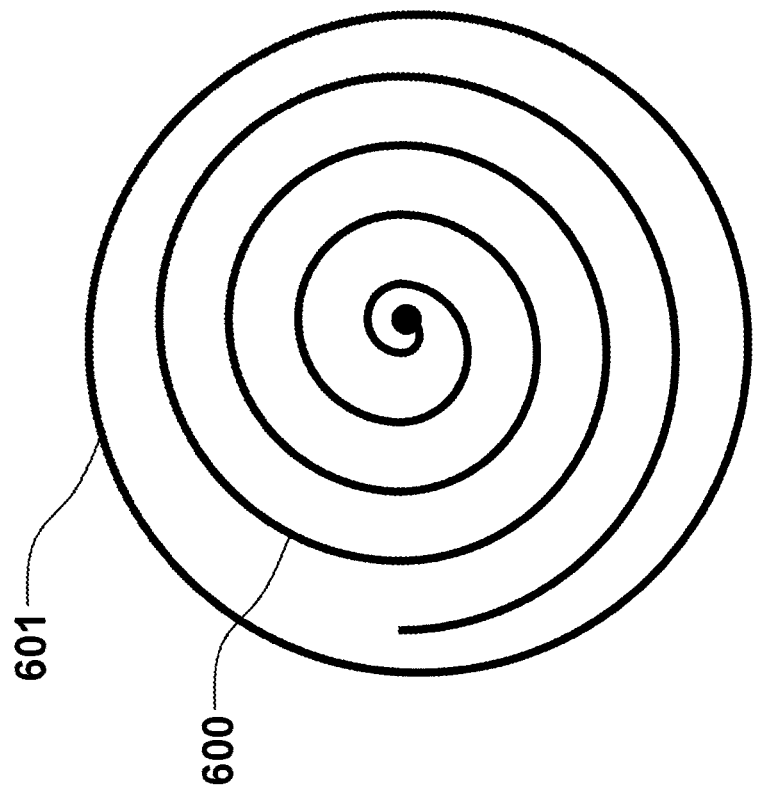
FIG. 17A is a drawing of another embodiment of a coupling element in the form of a spiral antenna.

FIG. 17A is a drawing of another embodiment of a coupling element for coupling evanescent waves in the form of a spiral antenna 600 consisting of a conductive spiral line on a ferrite substrate 601.

FIG. 17B is a drawing of another embodiment of a coupling element for coupling evanescent waves in the form of double spiral antenna 605 consisting of double spiral lines on a ferrite substrate 606.

Figure 18:
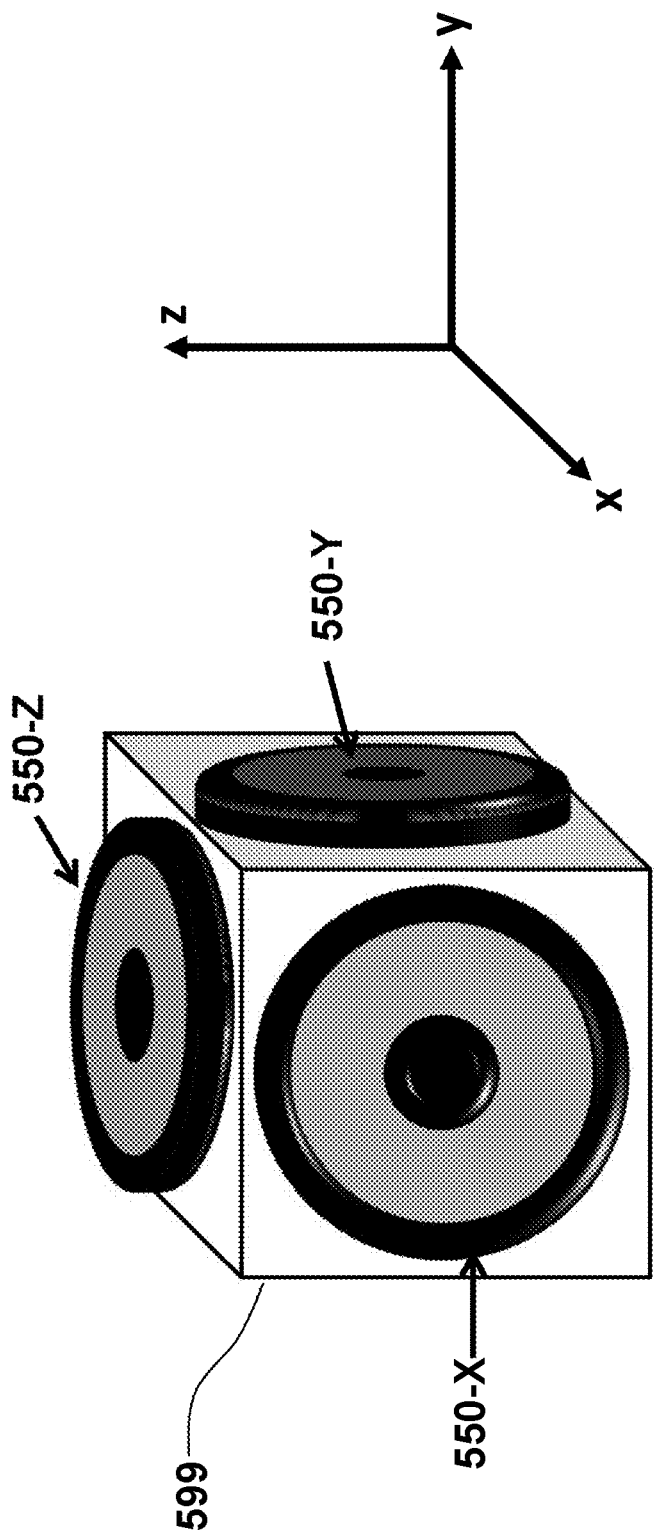
FIG. 18 is a drawing of a cube with three coaxial coupling elements similar to the one in FIG. 15A launching evanescent waves in X, Y, and Z directions.

FIG. 18 is a drawing of a cube 599 with three coaxial coupling elements similar to the one in FIG. 15A, coupling elements 550-X, 550-Y, and 550-Z, launching evanescent waves in X, Y, and Z directions. The RF power can be applied to each of the coupling elements using a similar system shown in FIG. 8B. RF power can be applied to each coupling element independently such that each coupling element can be turned on individually or in conjunction with one or the other two coupling elements. By changing the magnitude and/or phase of the RF power applied to the three coupling elements one can change the direction of the evanescent wave applied to the cube and effectively the distribution of the direction of the electric fields within the cube. While a cube is shown in the drawing this applies to the ability of applying evanescent waves to different shaped objects and controlling spatial distribution of the electric fields within that object. One clear advantage of using evanescent waves for applying electric field is that it is not necessary to have two electrodes on the opposite side of an object to apply the electric field to only a specific part of the object as this might not be possible in cases where one side of the object is not accessible or is too far way. This approach reduces the RF power needed to target a specific part of the body.

What is claimed is:

1. A method of selectively destroying or inhibiting a growth of rapidly dividing cells located within a target region of a patient, comprising:
   generating RF electromagnetic energy from an energy source;
   coupling the RF electromagnetic energy from the electromagnetic source to a coupling element;
   emitting an electromagnetic wave from the coupling element to the target region of the patient, the electromagnetic wave comprising a plurality of different electric field polarizations configured from the coupling element;
   causing formation of a selected polarization distribution using the plurality of different polarizations from the electric field through a spatial volume of the target region such that the selected polarization distribution, a frequency characteristic and a power characteristic of the electromagnetic wave cause damage to dividing cells in the target region while leaving the non-dividing cells spatially located within the target region substantially unharmed;
   wherein the coupling element comprises two or more coupling elements provided to couple RF energy to the target region with each coupling element launching an electromagnetic wave in the target region with the plurality of different electric field polarizations forming the selected polarization distribution configured from the coupling element;
   adjusting an amplitude and a phase of the RF energy applied to each of the coupling elements to form a time varying polarization distribution formed from the different polarizations; and
   switching one or more of the coupling elements from an on or off state to cause the different polarizations to be time varying to change the selected polarization distribution from a first polarization distribution to a second polarization distribution to cause damage to the dividing cells, while leaving the non-dividing cells unharmed.

2. The method of claim 1 wherein the RF energy is coupled to the target region via evanescent waves from the RF energy source.

3. The method of claim 1 wherein the coupling element is an aperture or an antenna or a wave-launcher.

4. The method of claim 1 wherein each of the coupling elements is positioned substantially perpendicular to another coupling element.

5. The method of claim 1 wherein the RF energy is coupled to the target region via a plurality of evanescent waves.

6. The method of claim 1 wherein at least two different frequencies are applied to the target region simultaneously or sequentially using one or more coupling elements.

7. A method of selectively destroying or inhibiting a growth of rapidly dividing cells located within a target region of a patient, comprising:
   generating RF electromagnetic energy from an energy source;
   coupling the RF electromagnetic energy from the electromagnetic source to a coupling element;
   emitting an electromagnetic wave from the coupling element to the target region of the patient, the electromagnetic wave comprising a plurality of different electric field polarizations configured from the coupling element;
   causing formation of a selected polarization distribution using the plurality of different polarizations from the electric field through a spatial volume of the target region such that the selected polarization distribution, a frequency characteristic and a power characteristic of the electromagnetic wave cause damage to dividing cells in the target region while leaving the non-dividing cells spatially located within the target region substantially unharmed;
   wherein the frequency of the RF source is between about 10 KHz and about 50 MHz and a strength of an electric field of the electromagnetic wave in at least a portion of the target region is at least 0.1 V/cm.

8. A method of selectively destroying or inhibiting a growth of rapidly dividing cells located within a target region of a patient, comprising:
   generating RF electromagnetic energy from an energy source;
   coupling the RF electromagnetic energy from the electromagnetic source to a coupling element;
   emitting an electromagnetic wave from the coupling element to the target region of the patient, the electromagnetic wave comprising a plurality of different electric field polarizations configured from the coupling element;
   causing formation of a selected polarization distribution using the plurality of different polarizations from the electric field through a spatial volume of the target region such that the selected polarization distribution, a frequency characteristic and a power characteristic of the electromagnetic wave cause damage to dividing cells in the target region while leaving the non-dividing cells spatially located within the target region substantially unharmed;
   wherein the frequency of the RF source is between about 100 KHz and about 300 KHz and a strength of an electric field of the electromagnetic wave in at least a portion of the target region is between about 1 V/cm and about 20 V/cm.

9. A method of selectively destroying or inhibiting a growth of rapidly dividing cells located within a target region of a patient, comprising:
   generating RF electromagnetic energy from an energy source;
   coupling the RF electromagnetic energy from the electromagnetic source to a coupling element;
   emitting an electromagnetic wave from the coupling element to the target region of the patient, the electromagnetic wave comprising a plurality of different electric field polarizations configured from the coupling element;
   causing formation of a selected polarization distribution using the plurality of different polarizations from the electric field through a spatial volume of the target region such that the selected polarization distribution, a frequency characteristic and a power characteristic of the electromagnetic wave cause damage to dividing cells in the target region while leaving the non-dividing cells spatially located within the target region substantially unharmed;

wherein the frequency of the RF source is between about 100 KHz and about 300 KHz and the RF power density in at least a portion of the target region is at least 1 mW/cm³.

10. A method of selectively destroying or inhibiting a growth of rapidly dividing cells located within a target region of a patient, comprising:

generating RF electromagnetic energy from an energy source;

coupling the RF electromagnetic energy from the electromagnetic source to a coupling element;

emitting an electromagnetic wave from the coupling element to the target region of the patient, the electromagnetic wave comprising a plurality of different electric field polarizations configured from the coupling element;

causing formation of a selected polarization distribution using the plurality of different polarizations from the electric field through a spatial volume of the target region such that the selected polarization distribution, a frequency characteristic and a power characteristic of the electromagnetic wave cause damage to dividing cells in the target region while leaving the non-dividing cells spatially located within the target region substantially unharmed;

wherein the coupling element comprises two or more coupling elements provided to couple RF energy to the target region with each coupling element launching an electromagnetic wave in the target region with the plurality of different electric field polarizations forming the selected polarization distribution configured from the coupling element; and adjusting an amplitude and a phase of the RF energy applied to each of the coupling elements to form a time varying polarization distribution formed from the different polarizations;

wherein the frequency of the applied RF energy is swept or stepped between two frequencies.

11. An apparatus for selectively destroying or inhibiting growth of rapidly dividing cells located within a target region of a patient, the apparatus comprising:

an RF source for generating an RF electromagnetic radiation;

a coupling element coupled to an output of the RF source and configured to receive the RF electromagnetic radiation and emit an electromagnetic wave from the coupling element to the target region of the patient, the coupling element configured to emit a plurality of different electric field polarizations from the electromagnetic wave causing formation of a selected polarization distribution using the plurality of different polarizations from the electromagnetic wave through a spatial volume of the target region;

a microcontroller coupled to the RF source and configured to adjust a power characteristic of the electromagnetic wave to form a time varying selected electric field polarization distribution such that the time varying selected polarization distribution of the electric field causes damage to dividing cells in the target region while leaving the non-dividing cells spatially located within the target region substantially unharmed;

wherein the RF source generates a frequency between about 10 KHz and about 50 MHz and a strength of an electric field of an electromagnetic wave in at least a portion of the target region is at least 0.1 V/cm.

12. An apparatus for selectively destroying or inhibiting growth of rapidly dividing cells located within a target region of a patient, the apparatus comprising:

an RF source for generating an RF electromagnetic radiation;

a coupling element coupled to an output of the RF source and configured to receive the RF electromagnetic radiation and emit an electromagnetic wave from the coupling element to the target region of the patient, the coupling element configured to emit a plurality of different electric field polarizations from the electromagnetic wave causing formation of a selected polarization distribution using the plurality of different polarizations from the electromagnetic wave through a spatial volume of the target region;

a microcontroller coupled to the RF source and configured to adjust a power characteristic of the electromagnetic wave to form a time varying selected electric field polarization distribution such that the time varying selected polarization distribution of the electric field causes damage to dividing cells in the target region while leaving the non-dividing cells spatially located within the target region substantially unharmed;

wherein the RF source generates a frequency between about 100 KHz and about 300 KHz and a strength of an electric field of an electromagnetic wave in at least a portion of the target region is between about 1 V/cm and about 20 V/cm.

13. An apparatus for selectively destroying or inhibiting growth of rapidly dividing cells located within a target region of a patient, the apparatus comprising:

an RF source for generating an RF electromagnetic radiation;

a coupling element coupled to an output of the RF source and configured to receive the RF electromagnetic radiation and emit an electromagnetic wave from the coupling element to the target region of the patient, the coupling element configured to emit a plurality of different electric field polarizations from the electromagnetic wave causing formation of a selected polarization distribution using the plurality of different polarizations from the electromagnetic wave through a spatial volume of the target region;

a microcontroller coupled to the RF source and configured to adjust a power characteristic of the electromagnetic wave to form a time varying selected electric field polarization distribution such that the time varying selected polarization distribution of the electric field causes damage to dividing cells in the target region while leaving the non-dividing cells spatially located within the target region substantially unharmed;

wherein the RF source generates a frequency between about 100 KHz and about 300 KHz and the RF power density in at least a portion of the target region is at least 1 mW/cm³.

14. A method of selectively destroying or inhibiting the growth of rapidly dividing cells located within a target region of a patient, comprising:

coupling RF energy from an RF source to the target region of the patient using three coupling elements oriented substantially perpendicular to each other;

emitting from each of the coupling elements an electromagnetic wave to the target region, the electromagnetic wave having a plurality of different electric field polarizations forming a polarization distribution from the plurality of different electric field polarizations spatially in the target region;

damaging a plurality of dividing cells in the target region using the electromagnetic wave having a plurality of frequency characteristics and a sufficient RF power to cause damage to dividing cells, while maintaining a plurality of non-dividing cells in the target region substantially unharmed while being subjected to the electromagnetic wave; and adjusting an amplitude and/or a phase of the RF energy coupled to each of the three coupling elements;

adjusting a time interval on initiating the emission of the electromagnetic wave from each of the coupling elements using a microcontroller coupled to each of the coupling elements; and adjusting dynamically a polarization and an amplitude of the electric field in the target region to time vary the polarization and the amplitude to cause further damage or kill a substantially maximum number of the dividing cells in the target region;

wherein the frequency of the RF source is between about 10 KHz and about 50 MHz and a strength of an electric field of the electromagnetic wave in at least a portion of the target region is at least 0.1 V/cm.

15. The method of claim 14 wherein at least two different frequencies are applied to the target region simultaneously or sequentially using one or more of the coupling elements.

16. The method of claim 14 wherein the RF energy is coupled to the target region via a plurality of evanescent waves.

17. The method of claim 14 wherein each of the coupling elements comprises an aperture or an antenna or a wave-launcher.

18. The method of claim 14 wherein the RF energy is pulsed, ramped, patterned, or constant.

19. The method of claim 14 further comprising using another treatment for the patient selected from at least chemotherapy, radiation therapy, or immunotherapy to kill cancer cells.

20. A method of selectively destroying or inhibiting the growth of rapidly dividing cells located within a target region of a patient, comprising:

coupling RF energy from an RF source to the target region of the patient using three coupling elements oriented substantially perpendicular to each other;

emitting from each of the coupling elements an electromagnetic wave to the target region, the electromagnetic wave having a plurality of different electric field polarizations forming a polarization distribution from the plurality of different electric field polarizations spatially in the target region;

damaging a plurality of dividing cells in the target region using the electromagnetic wave having a plurality of frequency characteristics and a sufficient RF power to cause damage to dividing cells, while maintaining a plurality of non-dividing cells in the target region substantially unharmed while being subjected to the electromagnetic wave; and adjusting an amplitude and/or a phase of the RF energy coupled to each of the three coupling elements;

adjusting a time interval on initiating the emission of the electromagnetic wave from each of the coupling elements using a microcontroller coupled to each of the coupling elements; and adjusting dynamically a polarization and an amplitude of the electric field in the target region to time vary the polarization and the amplitude to cause further damage or kill a substantially maximum number of the dividing cells in the target region;

wherein the frequency of the RF source is between about 100 KHz and about 300 KHz and a strength of an electric field of the electromagnetic wave in at least a portion of the target region is between about 1 V/cm and about 20 V/cm.

21. A method of selectively destroying or inhibiting the growth of rapidly dividing cells located within a target region of a patient, comprising:

coupling RF energy from an RF source to the target region of the patient using three coupling elements oriented substantially perpendicular to each other;

emitting from each of the coupling elements an electromagnetic wave to the target region, the electromagnetic wave having a plurality of different electric field polarizations forming a polarization distribution from the plurality of different electric field polarizations spatially in the target region;

damaging a plurality of dividing cells in the target region using the electromagnetic wave having a plurality of frequency characteristics and a sufficient RF power to cause damage to dividing cells, while maintaining a plurality of non-dividing cells in the target region substantially unharmed while being subjected to the electromagnetic wave; and adjusting an amplitude and/or a phase of the RF energy coupled to each of the three coupling elements;

adjusting a time interval on initiating the emission of the electromagnetic wave from each of the coupling elements using a microcontroller coupled to each of the coupling elements; and adjusting dynamically a polarization and an amplitude of the electric field in the target region to time vary the polarization and the amplitude to cause further damage or kill a substantially maximum number of the dividing cells in the target region;

wherein the frequency of the RF source is between about 100 KHz and about 300 KHz and an RF power density in at least a portion of the target region is at least 1 $mW/cm^3$.

* * * * *